(12) United States Patent
Wang et al.

(10) Patent No.: US 9,309,324 B2
(45) Date of Patent: Apr. 12, 2016

(54) OPTIMIZED MONOCLONAL ANTIBODIES AGAINST TISSUE FACTOR PATHWAY INHIBITOR (TFPI)

(75) Inventors: Zhuozhi Wang, Millbrae, CA (US); Junliang Pan, Moraga Town, CA (US); Joanna Grudzinska, Cologne (DE); Christian Votsmeier, Cologne (DE); Jan Tebbe, Cologne (DE); Joerg Birkenfeld, Duesseldorf (DE); Nina Wobst, Wuppertal (DE); Simone Brueckner, Cologne (DE); Susanne Steinig, Cologne (DE); Peter Scholz, Kleve (DE)

(73) Assignee: BAYER HEALTHCARE LLC, Tarrytown, NY (US)

( * ) Notice: Subject to any disclaimer, the term of this patent is extended or adjusted under 35 U.S.C. 154(b) by 0 days.

(21) Appl. No.: 13/582,401

(22) PCT Filed: Mar. 1, 2011

(86) PCT No.: PCT/US2011/026766
§ 371 (c)(1),
(2), (4) Date: Aug. 31, 2012

(87) PCT Pub. No.: WO2011/109452
PCT Pub. Date: Sep. 9, 2011

(65) Prior Publication Data
US 2012/0329996 A1    Dec. 27, 2012

Related U.S. Application Data

(60) Provisional application No. 61/309,290, filed on Mar. 1, 2010.

(51) Int. Cl.
*A61K 39/395* (2006.01)
*C07K 16/38* (2006.01)
*A61K 39/00* (2006.01)

(52) U.S. Cl.
CPC ........... *C07K 16/38* (2013.01); *A61K 2039/505* (2013.01); *C07K 2317/55* (2013.01); *C07K 2317/565* (2013.01); *C07K 2317/76* (2013.01); *C07K 2317/92* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 5,369,038 A | 11/1994 | Koike | |
| 5,902,582 A | 5/1999 | Hung | |
| 6,111,079 A | 8/2000 | Wylie | |
| 6,171,587 B1 | 1/2001 | Wun | |
| 6,423,316 B1 | 7/2002 | Riesbeck | |
| 6,593,291 B1 | 7/2003 | Green | |
| 6,656,746 B2 | 12/2003 | Sprecher | |
| 7,015,194 B2 | 3/2006 | Kjalke | |
| 8,481,030 B2 * | 7/2013 | Wang et al. | 424/133.1 |
| 2002/0031799 A1 | 3/2002 | Stafford | |
| 2002/0082206 A1 | 6/2002 | Leach | |
| 2002/0160934 A1 | 10/2002 | Broadus | |
| 2002/0197605 A1 | 12/2002 | Nakagawa | |
| 2003/0004324 A1 | 1/2003 | Rosen | |
| 2003/0028920 A1 | 2/2003 | Altier | |
| 2003/0059937 A1 | 3/2003 | Ruben | |
| 2003/0064491 A1 | 4/2003 | Farnet | |
| 2003/0157082 A1 | 8/2003 | Hunter | |
| 2003/0166004 A1 | 9/2003 | Gyuris | |
| 2003/0232054 A1 | 12/2003 | Tang | |
| 2003/0233675 A1 | 12/2003 | Cao | |
| 2004/0029129 A1 | 2/2004 | Wang | |
| 2004/0031072 A1 | 2/2004 | La Rosa | |
| 2004/0034888 A1 | 2/2004 | Liu | |
| 2004/0052799 A1 | 3/2004 | Smith | |
| 2004/0123343 A1 | 6/2004 | La Rosa | |
| 2004/0171538 A1 | 9/2004 | Sicard | |
| 2004/0172684 A1 | 9/2004 | Kovalic | |
| 2004/0214272 A1 | 10/2004 | La Rosa | |
| 2005/0004354 A1 | 1/2005 | Salfeld | |
| 2005/0058649 A1 | 3/2005 | Landes | |
| 2005/0108791 A1 | 5/2005 | Edgerton | |
| 2005/0118643 A1 | 6/2005 | Burgess | |
| 2005/0158313 A1 | 7/2005 | Rosen | |
| 2005/0186202 A1 | 8/2005 | Kashmiri | |
| 2005/0203280 A1 | 9/2005 | McMichael | |
| 2005/0208558 A1 | 9/2005 | Venter | |

(Continued)

FOREIGN PATENT DOCUMENTS

| | | |
|---|---|---|
| EP | 0539975 A1 | 5/1993 |
| JP | 06153985 | 6/1994 |

(Continued)

OTHER PUBLICATIONS

Janeway et al., Immunobiology, 3rd edition, 1997, Garland Press, pp. 3:1-3:11.*

(Continued)

*Primary Examiner* — Michael Szperka
(74) *Attorney, Agent, or Firm* — VLP Law Group LLP; Kurt T. Mulville

(57) ABSTRACT

Isolated monoclonal antibodies that bind human tissue factor pathway inhibitor (TFPI) are provided. Isolated nucleic acid molecules encoding monoclonal antibodies that bind TFPI are also contemplated. Pharmaceutical compositions comprising the anti-TFPI monoclonal antibodies and methods of treating deficiencies or defects in coagulation by administration of the antibodies are also provided. Methods of producing the antibodies are also provided.

10 Claims, 5 Drawing Sheets

(56) References Cited

U.S. PATENT DOCUMENTS

| | | |
|---|---|---|
| 2005/0260581 A1 | 11/2005 | Fontana |
| 2006/0003425 A1 | 1/2006 | Kroger |
| 2006/0019260 A1 | 1/2006 | Lerner |
| 2006/0024297 A1 | 2/2006 | Wood |
| 2006/0041961 A1 | 2/2006 | Abad |
| 2006/0068386 A1 | 3/2006 | Slesarev |
| 2006/0075522 A1 | 4/2006 | Cleveland |
| 2006/0107345 A1 | 5/2006 | Alexandrov |
| 2006/0234912 A1 | 10/2006 | Wang |
| 2006/0246071 A1 | 11/2006 | Green |
| 2006/0251658 A1 | 11/2006 | Ledbetter |
| 2006/0263363 A1 | 11/2006 | Ferlin |
| 2007/0020624 A1 | 1/2007 | Rubenfield |
| 2007/0020625 A1 | 1/2007 | Duchaud |
| 2007/0021600 A1 | 1/2007 | Doucette-Stamm |
| 2007/0042383 A1 | 2/2007 | Kapur |
| 2007/0044171 A1 | 2/2007 | Kovalic |
| 2007/0061916 A1 | 3/2007 | Kovalic |
| 2007/0065439 A1 | 3/2007 | Green |
| 2007/0072177 A1 | 3/2007 | Bakker |
| 2007/0083334 A1 | 4/2007 | Mintz |
| 2007/0118916 A1 | 5/2007 | Puzio |
| 2007/0202552 A1 | 8/2007 | Sidhu |
| 2007/0202566 A1 | 8/2007 | Bornscheuer |
| 2007/0224627 A1 | 9/2007 | Horowitz |
| 2007/0271630 A1 | 11/2007 | Boukharov |
| 2008/0008719 A1 | 1/2008 | Bowdish |
| 2008/0025980 A1 | 1/2008 | Hardy |
| 2008/0050774 A1 | 2/2008 | Berka |
| 2008/0095775 A1 | 4/2008 | Lewis |
| 2008/0148432 A1 | 6/2008 | Abad |
| 2008/0287309 A1 | 11/2008 | Bowdish |
| 2010/0173847 A1 | 7/2010 | Dockal |

FOREIGN PATENT DOCUMENTS

| | | |
|---|---|---|
| JP | 08075736 | 3/1996 |
| WO | WO 92/07584 | 5/1992 |
| WO | WO 97/09063 | 3/1997 |
| WO | WO 2005/055930 A2 | 6/2005 |
| WO | WO 2006/096345 A2 | 9/2006 |
| WO | WO 2010017196 A2 | 2/2010 |
| WO | WO 2010/071894 A2 | 6/2010 |
| WO | WO 2010072687 A1 | 7/2010 |
| WO | WO 2010072691 A1 | 7/2010 |

OTHER PUBLICATIONS

Rudikoff et al., Proc Natl Acad Sci USA, 1982, 79:1979-1983.*
Portolano et al., J. Immunol., 1993, 150:880-887.*
Fundamental Immunology, William E. Paul, M.D. ed., 3d ed. 1993, p. 242.*
PCT/US2009/052702, PCT Written Opinion of the International Searching Authority, Jun. 22, 2011.
Abumiya T, K-I Enjyoji, T Kokawa, Y-I Kamikubo and H Kato, *An Anti-Tissue Factor Pathway Inhibitor (TFPI) Monoclonal Antibody Recognized the Third Kunitz Domain (K3) of Free-Form TFPI but Not Lipoprotein-Associated Forms in Plasma*, 1995, J. Biochem. 118: 178-182.
Broze GJ JR., Tj Girard and WF Novotny, *The Lipoprotein-Associated Coagulation Inhibitor*, 1991, Progress in Hemostasis and Thrombosis 10: 243-268.
Broze, GJ JR., TJ Girard and WF Novotny, *Regulation of Coagulation by a Multivalent Kunitz-Type Inhibitor*, 1990, Biochemicstry 29(33): 7539-7546.
Burgering MJM, LPM Orbons, A Van Der Doelen, J Mulders, H JM Theunissen, PDJ Grootenhuis, W Bode, R Huber and MT Stubbs, *The Second Kunitz Domain of Human Tissue Factor Pathway Inhibitor: Cloning, Structure Determination and Interaction with Factor Xa*, 1997, J. Mol. Biol. 269:395-407.
Day KC, and DJ Welsch, *Bacterial Expression, Purification, and Partial Characterization of Amino Acids 94-155 of Human Tissue Factor Pathway Inhibitor (TFPI) as an Inhibitor of Blood Coagulation Factor Xa*, 1992, Thrombosis Research 68: 369-381.
Engelmann B, *Novel Initiation Mechanism of Blood Coagulation by Intravascular Tissue Factor*, Nov. 1, 2004, Blood, American Society of Hematology US, 104 (11) Part 2: 78B. (Abstract).
Erhardtsen E, M Ezban, MT Madsen, V Diness, S Glzer, U Hedner and O Nordfang, *Blocking of Tissue Factor Pathway Inhibitor (TFPI) Shortens the Bleeding Time in Rabbits with Antibody Induced Haemophilia A*, 1995, Blood Coagulation and Fibrinolysis 6: 388-394.
Girard TJ, D Gailani and GJ Broze, JR., *Complementary DNA Sequencing of Canine Tissue factor Pathway Inhibitor Reveals a Unique Nanomeric Repetitive Sequence between the Second and Third Kunitz Domains*, 1994, Biochem. J., 303: 923-928.
Girard TJ, LA Warren, WF Novotny, KM Likert, SG Brown, JP Miletich and GJ Bronze, JR., *Functional Significance of the Kunitz-type Inhibitory Domains of Lipoprotein-associated Coagulation Inhibitor*, 1989, Nature 338: 518-520.
Girard, TJ, R Eddy, RL Wesselschmidt, LA Macphail, KM Likert, MG Byers, TB Shows and GJ Bronze, JR., *Structure of the Human Lipoprotein-associated Coagulation Inhibitor Gene*, 1991, J. Biol. Chem. 266 (8): 5036-5041.
Houston DS, *Tissue Factor—A Therapeutic Target for Thrombotic Disorders*, 2002, Expert Opin. Ther. Targets, Apr. 6 (2): 159-174. (Abstract).
Jeske W, D Hoppensteadt, D Callas, MJ Koza and J Fareed, *Pharmacological Profiling of Recombinant Tissue Factor Pathway Inhibitor*, 1996, Seminars in Thrombosis and Hemostasis 22 (2): 213-219.
Kamei S, Y-I Kamikubo, T Hamuro, H Fujimoto, M Ishihara, H Yonemura, S Miyamoto, A Funatsu, F-I Enjyoji, T Abumiya T Miyata and H Kato, *Amino Acid Sequences and Inhibitory Activity of Rhesus Monkey Tissue Factor Pathway Inhibitor (TFPI): Comparison with Human TFPI*, 1994, J. Biochem. 115:708-714.
Mast AE, JE Stadanlick, JM Lockett, DJ Dietzen, KA Hasty and CL Hall, *Tissue Factor Pathway Inhibitor Binds to Platelet Thrombospondin-1*, 2000, J. Biol. Chem. (41): 31715-31721.
Østergaard PG, TC Beck, H Ørsted, A Svendsen, O Nordfang, PM Sandset, and J-B Hansen, *An Enzyme Linked Immunosorption Assay for Tissue Factor Pathway Inhibitor*, 1997, Thrombosis Research 87 (5): 447-459.
Petersen JGL, G Meyn, JS Rasmussen, J Petersen, SE Bjørn, I Jonassen, L Christiansen and O Nordfang, *Characterization of Human Tissue Factor Pathway Inhibitor Variants Expressed in Saccharomyces cerevisiae*, 1993, J. Biol. Chem. 268 (18): 13344-13351.
Petersen, LC, SE Bjørn, OH Olsen, ZO Nordfang, F Norris and K Norris, *Inhibitory Properties of Separate Recombinant Kunitz-type-protease-inhibitor Domains from Tissue-factor-pathway Inhibitor*, 1996, Eur. J. Biochem. 235: 310-316.
R&D Systems, R&D Systems New Products—Jun. 2007, http://www.rndsystems.co.uk Human TFPI Antibody, Monoclonal Mouse IgG2a Clone # 374720, Catalog No. MAB2974.
Reninger AJ, HFG Heijnen, H Schumann, H. M. Specht, W Schramm, and Z M. Ruggeri, *Mechanism of platelet adhesion to von Willebrand factor and microparticle formation under high shear stress*, 2006, Bloodjournal.Hematologylibrary.Org. vol. 7, #9.
Riesbeck K, A Dorling, G Kemball-Cook, JH McVey, M Jones, EGD Tuddenham and R I Lechler, *Human Tissue Factor Pathway Inhibitor Fused to CD4 Binds both FXa and TF/FVIIa at the Cell Surface*, 1997, Thromb. Haemost. 78:1488-1494.
Tang H, L. Ivanciu, N. Popescu, G Peer, E Hack, C Lupu, Fb Taylor Jr, and F. Lupu. *Sepsis-Induced Coagulation in the Baboon Lung Is Associated with Decreased Tissue Factor Pathway Inhibitor*, 2007, Am Journ. of Pathology vol. 171 #3.
rndsystems.tfpi "Human TFPI", Catalog No. DY2974.
Van 'T Veer C, TM Hackeng, C Delahaye, JJ Sixma, and BN Bouma, *Activated factor X and thrombin formation triggered by tissue factor on endothelial cell matrix in a flow model: effect of the tissue factor pathway inhibitor*, 1994 84: 1132-1142.
Warn-Cramer BJ and SL Maki, *Purification of Tissue Factor Pathway Inhibitor (TFPI) from Rabbit Plasma and Characterization of its Differences from TFPI isolated from Human Plasma*, 1992, Thrombosis Research 67: 367-383.

(56) References Cited

OTHER PUBLICATIONS

Welsch DJ, WF Novotny and T-C Wun, *Effect of Lipoprotein-Associated Coagulation Inhibitor (LACI) on Thromboplastin-Induced Coagulation of Normal and Hemophiliac Plasmas*, 1991, Thrombosis Research 64: 213-222.
Winkler K, A Kramer, G Kuttner, M. Seifert, C Scholz, H Wessner, J Schneider-Mergener, W Hohne, *Changing the Antigen binding specificity by Single Point Mutations of an Anti-p24 (HIV-1) Antibody*, 2000, Journ. of Immunology 165; 4505-4514.
Sevinsky J. R., L. Vijay Mohan Rao, and W. Ruf, *Ligand-Induced Protease Receptor Translocaiton into Caveloae: A Mechanism for Regulating Cell Surface Proteolysis of the Tissue Factor -Dependent Coagulation Pathway*, The Journal of Cell Biology, Apr. 1996, vol. 133, No. 2, pp. 293-304.
Tiemann, C, Brinkmann, T and Kleesiek. K, Detection of the Three Kunitz-Type Single Domains of Membrane-Bound Tissue Factor Pathway Inhibitor (TFPI) by Flow Cytometry, Eur J Chin Biochem 1997; 37(11): 855-860.
Casset, F., F. Roux, P. Mouchet, C. Bes, T. Chardes, C. Granier, J-C Mani, M. Pugnière, D. Laune, B. Pau, M. Kaczorek, R. Lahana, A. Rees, *A Peptide Mimetic of an Anti-CD4 Monoclonal Antibody by Rational Design*, Biochemical and Biophysical Research Communications, 307 (2003) 198-205.
Chen, Y., C. Wiesmann, G. Fuh, B. Li, H. W. Christinger, P. McKay, A. M. de Vos, H. B. Lowman, *Selection and Analysis of an Optimized Anti-VEGF Antibody: Crystal Structure of an Affinity-matured Fab in Complex with Antigen*, J. Mol. Biol. (1999) 293, 865-881.
Holm, P., R. Jafari, B. E. Sundström, *Functional mapping and single chain construction of the anti-cytokeratin 8 monoclonal antibody TS1*, Molecular Immunology 44 (2007) 1075-1084.
MacCallum, R., A.C.R. Martin, J. M. Thornton, *Antibody-antigen Interactions: Contact Analysis and Binding Site Topography*, J. Mol. Biol. (1996) 262, 732-745.
De Pascalis, R., M. Iwahashi, M. Tamura, E. A. Padlan, N. R. Gonzales, A. D. Santos, M. Giuliano, P. Schuck, J. Schlom, S. V. S. Kashmiri, *Grafting of "Abbreviated" Complementarity-Determining Regions Containing Specificity-Determining Residues Essential for Ligand and Contact to Engineer a Less Immunogenic Humanized Monoclonal Antibody*, The Journal of Immunology (2002) 169: 3076-3084.
Vajdos, F. F., C. W. Adams, T. N. Breece, L. G. Presta, A. M. de Vos, S. S. Sidhu, *Comprehensive Functional Maps of the Antigen-binding Site of an Anti-ErbB2 Antibody Obtained with Shotgun Scanning Mutagenesis*, J. Mol. Biol. (2002) 320, 415-428.
Wu, H., Y. Nie, W. D. Huse, J. D. Watkins, *Humanization of a Murine Monoclonal Antibody by Simultaneous Optimization of Framework and CDR Residues*, J. Mol. Biol. (1999) 294, 151-162.
Office Action, Chinese Application No. 200980134625.4, Apr. 23, 2013.
Office Action, Mexican Application No. MX/a2011/001351, May 6, 2014.
PCT/US2009/052702, International Search Report, Sep. 13, 2010.
PCT/US2009/052702, Report on Patentability, Feb. 8, 2011.
PCT/EP2009/067598, Written Opinion, Jun. 22, 2011.
Baugh RJ, Broze JR. GJ, and S Krishnaswamy, *Regulation of Extrinsic Pathway Factor Xa Formation by Tissue Factor Pathway Inhibitor*, 1998, J. Biol. Chem. 273(8): 4378-4386.
Brinkmann T, H Kähnert, W Prohaska, O Nordfang and K Kleesiek, *Synthesis of Tissue Factor Pathway Inhibitor in Human Synovial Cells and Chondrocytes Makes Joints the Predilected Site of Bleeding in Haemophiliacs*, 1994, Eur.J. Clin. Chem. Clin. Biochem. 32 (4): 313-317.
Browder T, Folkman J and S Pirie-Shepherd, *The Hemostatic System as a Regulator of Angiogenesis*, 2000, J. Biol. Chem. 275(3): 1521-1524.
Broze JR. GJ, *Tissue Factor Pathway Inhibitor and the Revised Theory of Coagulation*, 1995, Annu. Rev. Med. 46:103-112.
Campbell A.M., Monoclonal Antibody Technology, Elsevier Science Publishing Company, Inc., 1984, pp. 1-32.

Dahm AE, TO Andersen, F Rosendaal and PM Sandset, *A Novel Anticoagulant Activity Assay of Tissue Factor Pathway Inhibitor I (TFPI)*, J. Thromb.Haemost., 2005, 3 (4): 651-658.
Dockal M Pachlinger T, Hartmann R, Knappe S, Sorensen B, Wong MD, Conlan M, Cercele M, Bernstein B, Erlich HJ and F Scheiflinger, *Biological Explanation of Clinically Observed Elevation of TFPI Plasma Levels After Treatment with TFPI-Antagonistic Aptamer BAX 499*, 2012, Amer. Soc. Hematology, Abstract 1104, $54^{th}$ ASH Annual Meeting and Exposition.
Dockal M, Hartmann R, Fries M, Prohaska K, Pachlinger R, Polakowski T, Brandstetter J, Rosing J and F Scheiflinger, *Crystal Structure of Tissue Factor Pathway Inhibitor (TFPI Kunitz Domain 1 and 2 in Complex with an Inhibitory Cyclic Peptide*, 2013, Amer. Soc. Hematology, Abstract 453, $55^{th}$ ASH Annual Meeting and Exposition.
Dockal M, Hartmann R, Fries M, Thomassen MCLGD, Heinzmann A, Ehrlich H, Rosing J, Osterkamp F, Polakowski T, Reineke U, Griessner, Brandstetter H and F Scheiflinger, *Small Peptides Blocking Inhibition of Factor Xa and Tissue Factor-Factor VIIa by Tissue Factor Pathway Inhibitor (TFPI)*, 2014, J. Biol. Chem. 289(3): 1732-1741.
Dockal M, Hartmann R, Polakowski T, Brandstetter J, Kammlander W, Panholzer E, Redi C, Osterkapm, F, Rosing J and F Scheiflinger, *Design of a Most Efficient Inhibitor of TFPI by Molecular Fusion of Two Inhibitory Peptides*, 2013, Amer. Soc. Hematology, Abstract 3564, $55^{th}$ ASH Annual Meeting and Exposition.
Dockal M, Hartmann T, Polakowski T, Panhalzer E, Kammlander W, Osterkamp F, Reineke U, Schiviz A, Hoelriegl W and F Scheiflinger, *ATFPI Inhibitory Half Life Extended Fusion Peptide Proves Efficacy ini FVIII Knock Out Mice and Marmoset Monkeys*, 2014, Amer. Soc. Hematology, Abstract 1469, $56^{th}$ ASH Annual Meeting and Exposition.
Fitzgerald Industries International, #10R-T142A Monoclonal Mouse anti-TFPI antibody—product details, printed Dec. 9, 2014.
Forastiero RR, Martinuzzo and GJ Broze JR, *High Titers of Autoantibodies to Tissue Factor Pathway Inhibitor are Associated with the Antiphospholipid Syndrome*, 2003, J. Thrombosis and Haemostasis 1: 718-724.
GE Healthcare, Biacore Training Courses, *Kinetic and Affinity Analysis, Level 2*, extract, 1998.
Hansen J-B, Huseby KR, Huseby N-E, Ezban M and A Nordøy, *Tissue Factor Pathway Inhibitor in Complex with Low Density Lipoprotein Isolated from Human Plasma Does Not Possess Anticoagulant Function in Tissue Factor-Induced Coagulation* in Vitro, 1997, Thrombosis Research 85(5):413-425.
Higuchi DA, Wun TC, Likert Km and GJ Jr Broze, *The Effect of Leukocyte Elastase on Tissue Factor Pathway Inhibitor*, 1992, Blood 79: 1712-1719.
Horie S, Hiraishi S, Hirata Y, Kazama M and J Matsuda, *Oxidized Low-density Lipoprotein Impairs the Anti-coagulant Function of Tissue-Factor-Pathway Inhibitor Through Oxidative Modification by its High Association and Accelerated Degradation in Cultured Human Endothelial Cells*, 2000, Biochem. J. 352: 277-285.
Lindhout T, Willems G, Blezer R and HC Hemker, *Kinetics of the Inhibition of Human Factor Xa by Full-length and Truncated Recombinant Tissue Factor Pathway Inhibitor*, 1994, Biochm. J. 297: 131-136.
Liu T, Scallan Cd, Broze Jr GJ, Patarroyo-White S, Pierce GF and KE Johnson, *Improved Coagulation in Bleeding Disorders by Non-Anticoagulant Sulfated Polysaccharides (HASP)*, 2006, Thromb. Haemost. 95:68-76.
Maroney SA and AE Mast, *New Insights into the Biology of Tissue Factor Pathway Inhibitor*, 2015, J. Thrombosis and Haemostasis 13 (Suppl 1): S200-S207.
Martinuzzo M, Iglesias Varela ML, Adamczuk Y, Broze GJ and R Forastiero, *Antiphospholipid Antibodies and Antibodies to Tissue Factor Pathway Inhibitor in Women with Implantation Failures or Early and Late Pregnancy Losses*, 2005, J. Thromb. Haemost. 3: 2587-2589.
Maurissen LFA, *Characterization of Anticoagulant Functions of Protein S*, publically defended on Feb. 18, 2009, published in print 2009.

(56) References Cited

OTHER PUBLICATIONS

Myszka DG, *Improving Biosensor Analysis*, 1999, J. Mol. Recognit. 12:279-284.
Ndonwi M and Broze G Jr, *Protein S Enhances the Tissue Factor Pathway Inhibitor Inhibition of Factor Xa but not its Inhibition of Factor VIIa-Tissue Factor*, 2008, Thrombosis Haemostasis 6:1044-1046.
Ndonwi M, Tuley EA and GJ Broze Jr, *The Kunitz-3 Domain of TFPI-α is Required for Protein S-Dependent Enhancement of Factor Xa Inhibition*, 2010, Blood 116(8): 1344-1351.
Nordfang O, Valentin S Beck TC and U Hedner, *Inhibition of Extrinsic Pathway Inhibitor Shortens the Coagulation Time of Normal Plasma and of Hemophilia Plasma*, 1991, Thrombosis and Haemostasis 66(4): 464-467.
Novotny J, Handschumacher M, Haber E, Bruccoleri RE, Carlson WB, Fanning DW, Smith JA and GC Rose, *Antigenic Determinants in Proteins Coincide with Surface Regions Accessible to Large Probes (Antibody Domains)*, 1986, Proc. Natl. Acad. Sci. USA, 83:226-230.
Petersen LC, BJørn SE and O Nordfang, *Effect of Leukocyte Proteinases on Tissue Factor Pathway Inhibitor*, 1992, Thrombosis and Haemostasis 67(5): 537-541.
Petersen HH, *Experimental—Binding of mAbTFPI12021/NN mAb2021 and Bayer mAb2A8 to the isolated K2 Domain of TFPI*, 2015, Declaration, Novo Nordisk A/S, EP2379600B1 Opposition.
Petersen HH, *Experimental—Determination that Specific Monoclonal Antibodies are Capable of Binding to Individual Isolated Kunitz Domains of TFPI*, 2015, Declaration, Novo Nordisk A/S, EP2379600B1 Opposition.
Petersen HH, *Experimental—Kinetic Parameters for the Interaction between Full-Length TFPI with mAbTFPI2021/NN mAb2021, Bayer mAb2A8 and R&D Systems mAb2974*, 2015, Declaration, Novo Nordisk A/S, EP2379600B1 Opposition.
Pfizer Inc. Generated Technical Report on 2A8/TFPI Binding Location, in EP2379600 B2 Opposition filed by Pfizer, Oct. 22, 2014.
Pfizer Inc. Generated Technical Report on 2A8/TFPI K$D$, in EP2379600 B2 Opposition filed by Pfizer, Oct. 22, 2014.
Prasad S, Lillicrap D, Labelle A, Knappe S, Keller T, Burnett E, Powell S and KW Johnson, *Efficacy and Safety of a New-class Hemostatic Drug Candidate, AV513, in Dogs with Hemophilia A*, 2008, Blood 111(2): 672-679.
Protein Data Bank file 1ADZ, 1998.
Protein Data Bank file 1TFX, 1998.
Richards FM, *Calculation of Molecular Volumes and Areas for Structures of Known Geometry*, 1985, Methods in Enzymology, 115: 440-464.
Rocchia W, Alexov E and B Honig, *Extending the Applicability of the Nonlinear Poisson-Boltzmann Equation: Multiple Dielectric Constants and Multivalent Ions*, 2001, J. Phys. Chem. B 105:6507-6514.
Uni-ProtKB / Swiss-Prot entry P10646, Tissue Factor Pathway Inhibitor, online http://www.uniprot.org/uniprot/P10646, last modified Jan. 22, 2014.
Van Der Poll T, *Tissue Factor as an Initiator of Coagulation and Inflammation in the Lung*, 2008, Critical Care 12(Suppl 6): S3.
Willyard C, *Balancing Act—A Promising Therapy Curtails Clotting Inhibitors rather than Replacing Proteins that Promote Blood Clotting*, 2014, Nature 515: S168-S169.
Yang Y, HE X, Li J and H Shilin, *Preparation and Identification of a Monoclonal Antibody Against Tissue Factor Pathway Inhibitor*, 1997, Chin. J. Hematol. 18(3):118-122.
Zillmann A, Luther T, Müller I, Kotzsch M, Spannagl M, Kauke T, Oelschlägel, Zahler S and B Engelmann, *Platelet-Associated Tissue Factor Contributes to the Collagen-Triggered Activation of Blood Coagulation*, 2001, Biochem. Biophys. Res. Commun. 281:603-609.
Submission in European Opposition Proceeding of European Patent No. EP2379600, Aug. 11, 2015.

\* cited by examiner

| Number | Clone | Sample |
|---|---|---|
| 3 | HC_S31V | 2A8-3 |
| 9 | HC_K99L | 2A8-9 |
| 17 | LC_D91W | 2A8-17 |
| 20 | Wild type | 2A8 |

| Number | Clone | Sample |
|--------|---------|--------|
| 9 | HC_K99L | 2A8-9 |
| 10 | HC_K99V | |
| 17 | LC_D91W | 2A8-17 |
| 20 | Wild type | 2A8 |

OPTIMIZED MONOCLONAL ANTIBODIES AGAINST TISSUE FACTOR PATHWAY INHIBITOR (TFPI)

This application is a national phase of International Application No. PCT/US2011/026766, filed Mar. 1, 2011, which is claims the benefit of U.S. Provisional Application No. 61/309,290 filed Mar. 1, 2010.

SEQUENCE LISTING SUBMISSION

The Sequence Listing associated with this application is filed in electronic format via EFS-Web and hereby incorporated by reference into the specification in its entirety.

FIELD OF THE EMBODIMENTS

Provided are isolated monoclonal antibodies and fragments thereof that bind human tissue factor pathway inhibitor (TFPI).

BACKGROUND

Blood coagulation is a process by which blood forms stable clots to stop bleeding. The process involves a number of proenzymes and procofactors (or "coagulation factors") that are circulating in the blood. Those proenzymes and procofactors interact through several pathways through which they are converted, either sequentially or simultaneously, to the activated form. Ultimately, the process results in the activation of prothrombin to thrombin by activated Factor X (FXa) in the presence of Factor Va, ionic calcium, and platelets. The activated thrombin in turn induces platelet aggregation and converts fibrinogen into fibrin, which is then cross linked by activated Factor XIII (FXIIIa) to form a clot.

The process leading to the activation of Factor X can be carried out by two distinct pathways: the contact activation pathway (formerly known as the intrinsic pathway) and the tissue factor pathway (formerly known as the extrinsic pathway). It was previously thought that the coagulation cascade consisted of two pathways of equal importance joined to a common pathway. It is now known that the primary pathway for the initiation of blood coagulation is the tissue factor pathway.

Factor X can be activated by tissue factor (TF) in combination with activated Factor VII (FVIIa). The complex of Factor VIIa and its essential cofactor, TF, is a potent initiator of the clotting cascade.

The tissue factor pathway of coagulation is negatively controlled by tissue factor pathway inhibitor ("TFPI"). TFPI is a natural, FXa-dependent feedback inhibitor of the FVIIa/TF complex. It is a member of the multivalent Kunitz-type serine protease inhibitors. Physiologically, TFPI binds to activated Factor X (FXa) to form a heterodimeric complex, which subsequently interacts with the FVIIa/TF complex to inhibit its activity, thus shutting down the tissue factor pathway of coagulation. In principle, blocking TFPI activity can restore FXa and FVIIa/TF activity, thus prolonging the duration of action of the tissue factor pathway and amplifying the generation of FXa, which is the common defect in hemophilia A and B.

Indeed, some preliminary experimental evidence has indicated that blocking the TFPI activity by antibodies against TFPI normalizes the prolonged coagulation time or shortens the bleeding time. For instance, Nordfang et al. showed that the prolonged dilute prothrombin time of hemophilia plasma was normalized after treating the plasma with antibodies to TFPI (Thromb. Haemost., 1991, 66(4): 464-467). Similarly, Erhardtsen et al. showed that the bleeding time in hemophilia A rabbit model was significantly shortened by anti-TFPI antibodies (Blood Coagulation and Fibrinolysis, 1995, 6: 388-394). These studies suggest that inhibition of TFPI by anti-TFPI antibodies may be useful for the treatment of hemophilia A or B. Only polyclonal anti-TFPI antibody was used in these studies.

Using hybridoma techniques, monoclonal antibodies against recombinant human TFPI (rhTFPI) were prepared and identified. See Yang et al., Chin. Med. J., 1998, 111(8): 718-721. The effect of the monoclonal antibody on dilute prothrombin time (PT) and activated partial thromboplastin time (APTT) was tested. Experiments showed that anti-TFPI monoclonal antibody shortened dilute thromboplastin coagulation time of Factor IX deficient plasma. It is suggested that the tissue factor pathway plays an important role not only in physiological coagulation but also in hemorrhage of hemophilia (Yang et al., Hunan Yi Ke Da Xue Xue Bao, 1997, 22(4): 297-300).

Accordingly, antibodies specific for TFPI are needed for treating hematological diseases and cancer.

Generally, therapeutic antibodies for human diseases have been generated using genetic engineering to create murine, chimeric, humanized or fully human antibodies. Murine monoclonal antibodies were shown to have limited use as therapeutic agents because of a short serum half-life, an inability to trigger human effector functions, and the production of human antimouse-antibodies (Brekke and Sandlie, "Therapeutic Antibodies for Human Diseases at the Dawn of the Twenty-first Century," Nature 2, 53, 52-62, January 2003). Chimeric antibodies have been shown to give rise to human anti-chimeric antibody responses. Humanized antibodies further minimize the mouse component of antibodies. However, a fully human antibody avoids the immunogenicity associated with murine elements completely. Thus, there is a need to develop fully human antibodies to avoid the immunogenicity associated with other forms of genetically engineered monoclonal antibodies. In particular, chronic prophylactic treatment such as would be required for hemophilia treatment with an anti-TFPI monoclonal antibody has a high risk of development of an immune response to the therapy if an antibody with a murine component or murine origin is used due to the frequent dosing required and the long duration of therapy. For example, antibody therapy for hemophilia A may require weekly dosing for the lifetime of a patient. This would be a continual challenge to the immune system. Thus, the need exists for a fully human antibody for antibody therapy for hemophilia and related genetic and acquired deficiencies or defects in coagulation.

Therapeutic antibodies have been made through hybridoma technology described by Koehler and Milstein in "Continuous Cultures of Fused Cells Secreting Antibody of Predefined Specificity," Nature 256, 495-497 (1975). Fully human antibodies may also be made recombinantly in prokaryotes and eukaryotes. Recombinant production of an antibody in a host cell rather than hybridoma production is preferred for a therapeutic antibody. Recombinant production has the advantages of greater product consistency, likely higher production level, and a controlled manufacture that minimizes or eliminates the presence of animal-derived proteins. For these reasons, it is desirable to have a recombinantly produced monoclonal anti-TFPI antibody.

In addition, because TFPI binds to activated Factor X (FXa) with high affinity, an effective anti-TFPI antibody should have a comparable affinity. Thus, it is desirable to have an anti-TFPI antibody which has binding affinity which can compete with TFPI/FXa binding.

SUMMARY

Monoclonal antibodies to human tissue factor pathway inhibitor (TFPI) are provided. Further provided are the isolated nucleic acid molecules encoding the same. Pharmaceutical compositions comprising the anti-TFPI monoclonal antibodies and methods of treatment of genetic and acquired deficiencies or defects in coagulation such as hemophilia A and B are also provided. Also provided are methods for shortening the bleeding time by administering an anti-TFPI monoclonal antibody to a patient in need thereof. Methods for producing a monoclonal antibody that binds human TFPI according to the present invention are also provided.

In some embodiments, the monoclonal antibodies to TFPI provided have been optimized, for example to have increased affinity or increased functional activity.

DETAILED DESCRIPTION

Definitions

Figure 1:
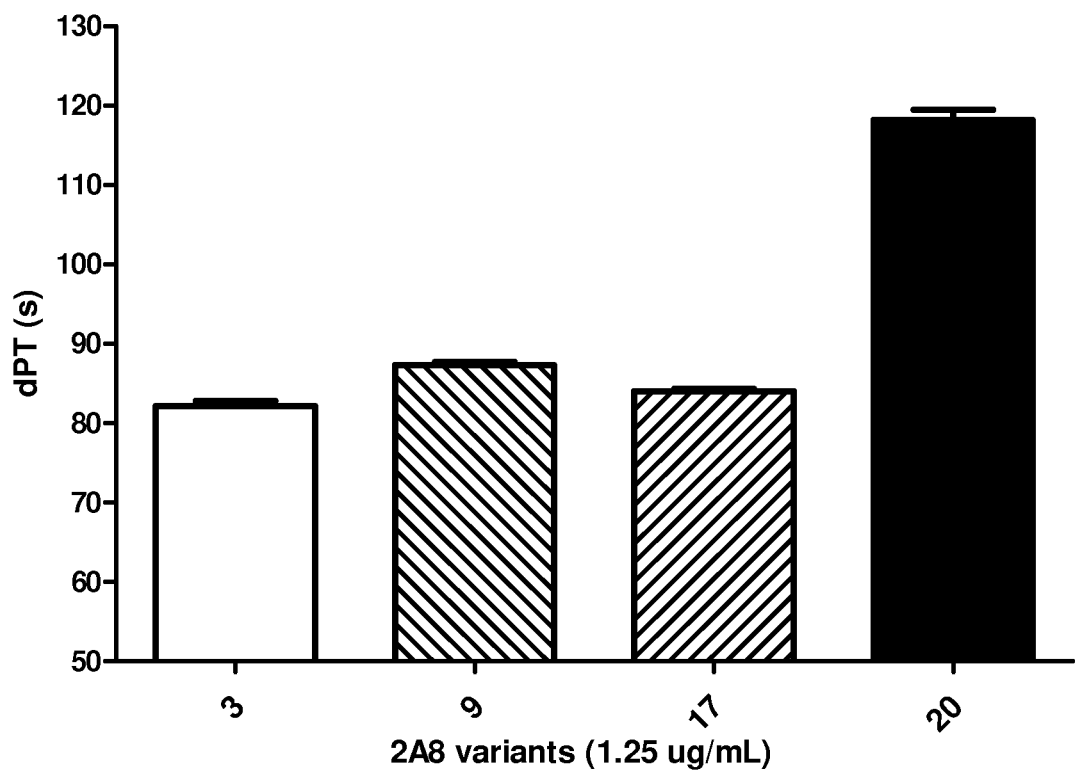
FIG. 1 depicts a bar graph illustrating selected 2A8 variants with single amino acid substitutions which showed more potency in shortening clotting time in human hemophilia A plasma using a dPT assay.

The term "tissue factor pathway inhibitor" or "TFPI" as used herein refers to any variant, isoform and species homolog of human TFPI that is naturally expressed by cells. In a preferred embodiment of the invention, the binding of an antibody of the invention to TFPI reduces the blood clotting time.

As used herein, an "antibody" refers to a whole antibody and any antigen binding fragment (i.e., "antigen-binding portion") or single chain thereof. The term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-TFPI monoclonal antibody fragment binds to an epitope of TFPI. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); (vii) minibodies, diaboidies, triabodies, tetrabodies, and kappa bodies (see, e.g. Ill et al., Protein Eng 1997; 10:949-57); (viii) camel IgG; and (ix) IgNAR. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are analyzed for utility in the same manner as are intact antibodies.

Furthermore, it is contemplated that an antigen binding fragment may be encompassed in an antibody mimetic. The term "antibody mimetic" or "mimetic" as used herein is meant a protein that exhibits binding similar to an antibody but is a smaller alternative antibody or a non-antibody protein. Such antibody mimetic may be comprised in a scaffold. The term "scaffold" refers to a polypeptide platform for the engineering of new products with tailored functions and characteristics.

As used herein, the terms "inhibits binding" and "blocks binding" (e.g., referring to inhibition/blocking of binding of TFPI ligand to TFPI) are used interchangeably and encompass both partial and complete inhibition or blocking. Inhibition and blocking are also intended to include any measurable decrease in the binding affinity of TFPI to a physiological substrate when in contact with an anti-TFPI antibody as compared to TFPI not in contact with an anti-TFPI antibody, e.g., the blocking of the interaction of TFPI with factor Xa or blocking the interaction of a TFPI-factor Xa complex with tissue factor, factor VIIa or the complex of tissue factor/factor VIIa by at least about 10%, 20%, 30%, 40%, 50%, 60%, 70%, 80%, 90%, 95%, 96%, 97%, 98%, 99%, or 100%.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

An "isolated antibody," as used herein, is intended to refer to an antibody which is substantially free of other antibodies having different antigenic specificities (e.g., an isolated antibody that binds to TFPI is substantially free of antibodies that bind antigens other than TFPI). An isolated antibody that binds to an epitope, isoform or variant of human TFPI may, however, have cross-reactivity to other related antigens, e.g., from other species (e.g., TFPI species homologs). Moreover, an isolated antibody may be substantially free of other cellular material and/or chemicals.

As used herein, "specific binding" refers to antibody binding to a predetermined antigen. Typically, the antibody binds with an affinity of at least about $10^5$ $M^{-1}$ and binds to the predetermined antigen with an affinity that is higher, for example at least two-fold greater, than its affinity for binding to an irrelevant antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "high affinity" for an IgG antibody refers to a binding affinity of at least about $10^7 M^{-1}$, in some embodiments at least about $10^8 M^{-1}$, in some embodiments at least about $10^9 M^{-1}$, $10^{10} M^{-1}$, $10^1 M^{-1}$ or greater, e.g., up to $10^{13} M^{-1}$ or greater. However, "high affinity" binding can vary for other antibody isotypes. For example, "high affinity" binding for an IgM isotype refers to a binding affinity of at least about $1.0 \times 10^7 M^{-1}$. As used herein, "isotype" refers to the antibody class (e.g., IgM or IgG1) that is encoded by heavy chain constant region genes.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). It is envisioned that the antibodies of the present invention may have conservative amino acid substitutions and still retain activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, preferably about 90%, 91%, 92%, 93%, 94%, or 95%, more preferably at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. The invention includes nucleic acid sequences and polypeptide sequences having substantial homology to the specific nucleic acid sequences and amino acid sequences recited herein.

The percent identity between two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40. Further details found at: Invitrogen's website for LINNEA Communities, Vector TFI Community, AlignX module for Vector NTI.

Another method for determining the best overall match between a query sequence (a sequence of the present invention) and a subject sequence, also referred to as a global sequence alignment, can be determined using the CLUSTALW computer program (Thompson et al., Nucleic Acids Research, 1994, 2(22): 4673-4680), which is based on the algorithm of Higgins et al., (Computer Applications in the Biosciences (CABIOS), 1992, 8(2): 189-191). In a sequence alignment the query and subject sequences are both DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters are preferred: Gap Opening Penalty=10, Gap Extension Parameter=0.05; Gap Separation Penalty Range=8; % Identity for Alignment Delay=40.

The nucleic acids may be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following may be used: alkaline/SDS treatment, CsCl banding, column chromatography, agarose gel electrophoresis and others well known in the art.

Monoclonal Antibodies Optimized for High Affinity and Functional Activity

Several anti-TFPI antibodies were identified in a previous study and described in PCT Application No. PCT/US2009/052702 filed 4 Aug. 2009, hereby incorporated by reference for all purposes. These anti-TFPI antibodies may be further optimized, for example by improving their affinity and blocking activity to TFPI. Such optimization can be performed for example by utilizing site saturation mutagenesis of the complementarity determining regions (CDRs) or residues in close proximity to the CDRs, i.e. about 3 or 4 residues adjacent to the CDRs, of the antibodies.

Also provided are monoclonal antibodies having increased or high affinity to TFPI. In some embodiments, the anti-TFPI antibodies have a binding affinity of at least about $10^7 M^{-1}$, in some embodiments at least about $10^8 M^{-1}$, in some embodiments at least about $10^9 M^{-1}$, $10^{10} M^{-1}$, $10^{11} M^{-1}$ or greater, e.g., up to $10^{13} M^{-1}$ or greater.

Site saturation mutagenesis in and adjacent to the CDRs of two anti-TFPI parental antibodies, designated herein as 2A8 and 4B7, was utilized to optimize the antibodies for affinity and functional activity. It is also contemplated that the same optimization may be performed on any of the antibodies described in the previous PCT/US2009/052702.

In some embodiments, site saturation mutagenesis of the CDRs may be done on the anti-TFPI antibodies. For 2A8, the CDRs in the heavy chain shown in SEQ ID NO:1 correspond to residues FTFRSYGMS (residues 27 to 35) (SEQ ID NO: 35), SIRGSSSSTYYADSVKG (residues 50 to 66) (SEQ ID NO: 36), and KYRYWFDY (residues 99 to 106) (SEQ ID NO 37). For the 2A8 light chain shown in SEQ ID NO:2, the CDRs correspond to residues SGDNLRNYYAH (residues 23 to 33) (SEQ ID NO: 38), YYDNNRPS (residues 48 to 55) (SEQ ID NO: 39), and QSWDDGVPV (residues 88 to 96) (SEQ ID NO: 40). For 4B7, the CDRs in the heavy chain shown in SEQ ID NO: 3 correspond to residues DSVSSNSAAWS (residues 27 to 37) (SEQ ID NO: 41), IIYKRSKWYNDYAVSVKS (residues 52 to 70) (SEQ ID NO: 42), and WHSDKHWGFDY (residues 102 to 112) (SEQ ID NO: 43). For the 4B7 light chain shown in SEQ ID NO:4, the CDRs correspond to residues RSSQSLVFSDGNTYLN (residues 24 to 39) (SEQ ID NO: 44), KGSNRAS (residues 55 to 61) (SEQ ID NO: 45), and QQYDSYPLT (residues 94 to 102) (SEQ ID NO: 46) of SEQ ID NO: 4. A modification may be made in any of the six CDRs individually or combinations of modifications may be made. Further, two or more modifications may be made in a single CDR. In other embodiments, modifications may also be introduced in close proximity to the CDRs, for example about 3 or 4 residues on either side of each CDR.

Briefly, single and/or multiple amino acid modifications were introduced and analyzed to optimize, e.g. improve the affinity, of parental antibodies 2A8 and 4B7. First, single amino acid modifications were introduced into the six CDRs or adjacent to the CDRs of each antibody followed by analysis of TFPI-binding properties. Modifications that increased binding signal to TFPI were selected for combination with one or more other modifications and analyzed for further increase of the binding signal. After each analysis, selected antibody variants were used to measure their affinity to TFPI and activity in blocking TFPI activity and shortening clotting time. Thus, in some embodiments, provided is an isolated monoclonal antibody that binds to human tissue factor pathway inhibitor having increased affinity to TFPI as compared to the unmodified parental antibodies. Further, in some embodiments, provided is an isolated monoclonal antibody that binds to human tissue factor pathway inhibitor having increased blocking activity of TFPI as compared to the unmodified parental antibodies. In some embodiments, provided is an isolated monoclonal antibody that binds to human tissue factor pathway inhibitor having a shortened clotting time as compared to the unmodified parental antibodies.

In some embodiments, additional amino acid modifications were introduced to reduce divergence from the germline sequence. In other embodiments, amino acid modifications were introduced to facilitate antibody production for large scale production processes.

The antibody may be species specific or may cross react with multiple species. In some embodiments, the antibody may specifically react or cross react with TFPI of human, mouse, rat, rabbit, guinea pig, monkey, pig, dog, cat or other mammalian species.

The antibody may be of any of the various classes of antibodies, such as without limitation an IgG1, an IgG2, an IgG3, an IgG4, an IgM, an IgA1, an IgA2, a secretory IgA, an IgD, and an IgE antibody.

In one embodiment, provided is an isolated fully human monoclonal antibody to human tissue factor pathway inhibitor.

In another embodiment, provided is an isolated fully human monoclonal antibody to Kunitz domain 2 of human tissue factor pathway inhibitor.

2A8 Variants

Accordingly, in some embodiments, provided is an isolated monoclonal antibody that binds to human tissue factor pathway inhibitor, wherein the antibody comprises a heavy chain comprising an amino acid sequence shown in SEQ ID NO:1, wherein said amino acid sequence comprises one or more amino acid modifications. In some embodiments, the modification of the heavy chain of 2A8 is a substitution, an insertion or a deletion.

In some embodiments, the substitutions are located in the CDRs of the heavy chain of 2A8. In other embodiments, the substitutions are located outside the CDRs of the heavy chain of 2A8.

In some embodiments, the substitution of the heavy chain of 2A8 is at a position selected from S31, G33, S35, I51, S54, S55, K99 and F104. In some embodiments, the substitution of the heavy chain of 2A8 may also include a position selected from Q1, R30, M34, S50, R52 and S56. For example, the substitution may be selected from Q1E, R30S, S31P, S31V, G33A, G33K, G33P, M34I, M34K, S35L, S35D, S50A, I51D, I51E, R52S, S54F, S54D, S55A, S55G, S55R, S56G, K99V, K99L, and F104Y. Further, in some embodiments, the antibody may comprise two or more substitutions selected from Q1E, R30S, S31P, S31V, G33A, G33K, G33P, M34I, M34K, S35L, S35D, S50A, I51D, I51E, R52S, S54F, S54D, S55A, S55G, S55R, S56G, K99V, K99L, and F104Y.

In some embodiments, the heavy chain of 2A8 has the following substitutions relative to SEQ ID NO:1: S31V+I51D+S54F+K99V; G33P+S35D+S54F+K99L; S35D+I51D+S55R+K99V; S35L+S54F+K99V; S31V+G33P+S35D; S35D+I51D+K99L; S31V+I51D+S55R+K99L; S31V+S35D+I51D+K99V; G33P+I51D+S54F; I51D+S54F+K99L; S35D+K99L; S31V+G33P+I51D+S54F+K99V; S35D+I51E+S55R+K99L; S31V+K99V; S31V+I51E+S55R+K99V; S35D+S55R+K99L; S31V+S54F+K99L; S31V+I51D+S55R+K99V; S31V+S35D+S55R; S31V+S35D; S31V+I51D+S55R; S35D+S54F+S55R+K99L; S31V+S35D+S54F S31V+S35L+I51D+S54F+K99V; and S31V+S35L+I51E+S54F+K99V.

In some embodiments, the heavy chain of 2A8 has the following substitutions relative to SEQ ID NO:1: G33A+S35D+S55R+K99L; G33P+I51D+S54F; G33P+S35D+S54F+K99L; I51D+S54F+K99L; M34I+S35D+S55R+K99L; M34K+S35D+S55R+K99L; Q1E+R30S+S35D+S55G+S56G+K99L; Q1E+R30S+S35D+S55R+S56G+K99L;
Q1E+S31V+S50A+I51D+S55R+S56G+K99V; Q1E+S35D+S55R+K99L; R30S+S31V+I51D+S55R+K99V; R30S+S35D+S55R+K99L; S31V+G33A+I51D+S55R+K99V; S31V+G33P+I51D+S54F+K99V; S31V+G33P+S35D; S31V+I51D+R52S+S55R+K99V; S31V+I51D+S54F+K99V; S31V+I51D+S55R; S31V+I51D+S55R+K99L; S31V+I51D+S55R+K99V; S31V+I51D+S55R+S56G+K99V; S31V+I51E+S55R+K99V; S31V+K99V; S31V+S35D; S31V+S35D+I51D+K99V; S31V+S35D+S54F; S31V+S35D+S55R; S31V+S35L+I51D+S54F+K99V; S31V+S35L+I51E+S54F+K99V; S31V+S50A+

I51D+S55R+K99V; S31V+S54F+K99L; S35D+I51D+ K99L; S35D+I51D+S55R+K99V; S35D+I51E+S55R+ K99L; S35D+K99L; S35D+R52S+K99L; S35D+R52S+ S55R+K99L; S35D+S50A+K99L; S35D+S50A+S55R+ K99L; S35D+S54F+S55R+K99L; S35D+S55G+K99L; S35D+S55R+K99L; S35D+S55R+S56G+K99L; S35D+ S56G+K99L; and S35L+S54F+K99V.

In some embodiments, the heavy chain of 2A8 has one or more deletions. In some embodiments, the deletions are located in the CDRs of the heavy chain of 2A8. In other embodiments, the deletions are located outside the CDRs of the heavy chain of 2A8. In some embodiments, for example, the deletion is at a position selected from I51, S56 and S57.

Further, provided is an isolated monoclonal antibody that binds to human tissue factor pathway inhibitor, wherein the antibody comprises a light chain comprising an amino acid sequence shown in SEQ ID NO:2, wherein said amino acid sequence comprises one or more amino acid modifications. In some embodiments, the modification is a substitution, an insertion or a deletion.

In some embodiments, the substitutions are located in the CDRs of the light chain of 2A8. In other embodiments, the substitutions are located outside the CDRs of the light chain of 2A8.

In some embodiments, the substitution of the light chain of 2A8 is at a position selected from A32, Y48, N51, N52, P54, D91, D92 and V96. In some embodiments, the substitution of the light chain of 2A8 may also include a position selected from D1, I2, A13, S21, N26, R28, N29, H33, Y49, G56, E80, S89, G93, V94 and P95. For example, the substitution may be selected from D1S, I2Y, A13S, S21T, N26A, R28P, N29K, A32N, H33Y, Y48F, Y49R, N51S, N51V, N52G, P54L, G56D, E80M, S89A, D91L, D91R, D91W, D91K, D92S, D92T, G93S, V94T, P95V, P95A, V96G, V96M and V96W. Further, in some embodiments, the antibody may comprise two or more substitutions selected from D1S, I2Y, A13S, S21T, N26A, R28P, N29K, A32N, H33Y, Y48F, Y49R, N51S, N51V, N52G, P54L, G56D, E80M, S89A, D91L, D91R, D91W, D91K, D92S, D92T, G93S, V94T, P95V, P95A, V96G, V96M and V96W.

In some embodiments, the light chain of 2A8 has the following substitutions relative to SEQ ID NO:2: Y48F+N51V; Y48F+N52G; Y48F+D91K; Y48F+D91L+V96W; Y48F+ D91W; Y48F+N52G+D91L+V96W; Y48F+N51V+V96W; D91L+V96W; Y48F+N51V+D91W; Y48F+N51V+D91L+ V96W; N51V+D91W; Y48F+N51V+G56D+V96W; Y48F+ N51V+D91L; and N51V+D91K.

In some embodiments, the light chain of 2A8 has the following substitutions relative to SEQ ID NO:2: A13S+Y48F+ N51V+D91W;
D1S+I2Y+A13S+S21T+R28P+N29K+Y48F+E80M+ D91L+D92S+V94T+V96W; D1S+I2Y+A13S+S21T+ R28P+N29K+Y48F+N51S+E80M+D91L+D92S+V94T+ V96W; D1S+I2Y+A13S+S21T+R28P+N29K+Y48F+ N51V+E80M+D91W; D1S+I2Y+A13S+S21T+R28P+ N29K+Y48F+N51V+E80M+S89A+D91W+D92S+G93S+ V94T;
D1S+I2Y+A13S+S21T+R28P+N29K+Y48F+Y49R+ N51S+E80M+D91L+D92S+V94T+V96W; D1S+I2Y+ A13S+S21T+R28P+Y48F+N51V+E80M+D91W; D1S+ I2Y+A13S+S21T+R28P+Y48F+N51V+E80M+S89A+ D91W+D92S+G93S+V94T; D1S+Y48F+N51V+D91W; D91L+V96W; H33Y+Y48F+N51V+D91W; I2Y+Y48F+ N51V+D91W; N26A+Y48F+N51V+D91W; N29K+Y48F+ N51V+D91W; N51V+D91K; N51V+D91W; R28P+Y48F+ N51V+D91W; S21T+Y48F+N51V+D91W; Y48F+D91K; Y48F+D91L+D92S+V96W; Y48F+D91L+G93S+V96W; Y48F+D91L+P95V+V96W; Y48F+D91L+V94T+V96W; Y48F+D91L+V96W; Y48F+D91W; Y48F+N51S+D91L+ V96W; Y48F+N51V; Y48F+N51V+D91L; Y48F+N51V+ D91L+V96W; Y48F+N51V+D91W; Y48F+N51V+D91W+ D92S; Y48F+N51V+D91W+G93S; Y48F+N51V+D91W+ P95V; Y48F+N51V+D91W+V94T; Y48F+N51V+E80M+ D91W; Y48F+N51V+G56D+V96W; Y48F+N51V+S89A+ D91W; Y48F+N51V+S89A+D91W+D92S+G93S+V94T+ P95A; Y48F+N51V+V96W; Y48F+N52G; Y48F+N52G+ D91L+V96W; and Y48F+S89A+D91L+V96W.

Also provided is an isolated monoclonal antibody that binds to human tissue factor pathway inhibitor, wherein the antibody comprises: a) a heavy chain comprising an amino acid sequence shown in SEQ ID NO:1, wherein said heavy chain amino acid sequence comprises one or more amino acid modifications; and b) a light chain comprising an amino acid sequence shown in SEQ ID NO:2, wherein said light chain amino acid sequence comprises one or more amino acid modifications. Examples of modifications that can be made are provided above.

In some embodiments, the isolated monoclonal antibody that binds to human tissue factor pathway inhibitor comprises a heavy chain comprising an amino acid sequence selected from SEQ ID NO: 5, 6, 7, 8, 9, 10, and 11.

In some embodiments, the isolated monoclonal antibody that binds to human tissue factor pathway inhibitor comprises a light chain comprising an amino acid sequence selected from SEQ ID NO: 12, 13, 14, 15, 16, 17, and 18.

In some embodiments, the isolated monoclonal antibody that binds to human tissue factor pathway inhibitor comprises: a) a heavy chain comprising an amino acid sequence selected from SEQ ID NO: 5, 6, 7, 8, 9, 10, and 11; and b) a light chain comprising an amino acid sequence selected from SEQ ID NO: 12, 13, 14, 15, 16, 17, and 18. In some embodiments, the isolated monoclonal antibody that binds to human tissue factor pathway inhibitor comprises: a) a heavy chain comprising an amino acid sequence shown in SEQ ID NO: 5; and b) a light chain comprising an amino acid sequence shown in SEQ ID NO: 12. In some embodiments, the isolated monoclonal antibody that binds to human tissue factor pathway inhibitor comprises: a) a heavy chain comprising an amino acid sequence shown in SEQ ID NO: 6; and b) a light chain comprising an amino acid sequence shown in SEQ ID NO: 13. In some embodiments, the isolated monoclonal antibody that binds to human tissue factor pathway inhibitor comprises: a) a heavy chain comprising an amino acid sequence shown in SEQ ID NO: 7; and b) a light chain comprising an amino acid sequence shown in SEQ ID NO: 14. In some embodiments, the isolated monoclonal antibody that binds to human tissue factor pathway inhibitor comprises: a) a heavy chain comprising an amino acid sequence shown in SEQ ID NO: 8; and b) a light chain comprising an amino acid sequence shown in SEQ ID NO: 15. In some embodiments, the isolated monoclonal antibody that binds to human tissue factor pathway inhibitor comprises: a) a heavy chain comprising an amino acid sequence shown in SEQ ID NO: 9; and b) a light chain comprising an amino acid sequence shown in SEQ ID NO: 16. In some embodiments, the isolated monoclonal antibody that binds to human tissue factor pathway inhibitor comprises: a) a heavy chain comprising an amino acid sequence shown in SEQ ID NO: 10; and b) a light chain comprising an amino acid sequence shown in SEQ ID NO: 17. In some embodiments, the isolated monoclonal antibody that binds to human tissue factor pathway inhibitor comprises: a) a heavy chain comprising an amino acid sequence shown in SEQ ID NO: 11; and b) a light chain comprising an amino acid sequence shown in SEQ ID NO: 18.

4B7 Variants

Also provided is an isolated monoclonal antibody that binds to human tissue factor pathway inhibitor, wherein the antibody comprises an amino acid sequence shown in SEQ ID NO:3 comprising one or more amino acid modifications. In some embodiments, the modification of the heavy chain of 4B7 is a substitution, an insertion or a deletion.

In some embodiments, the substitutions are located in the CDRs of the heavy chain of 4B7. In other embodiments, the substitutions are located outside the CDRs of the heavy chain of 4B7.

In some embodiments, the substitution of the heavy chain of 4B7 is at a position selected from S30, N32, S57, K58, N61, D62, H103, H107, G109 and Y112. In some embodiments, the substitution of the heavy chain of 4B7 may also include a position selected from Q1, S37, G44, I53 and K55. For example, the substitution may be selected from Q1E, S30R, N32D, N32E, S33G, S37N, G44S, I53T, K55Y, S57K, S57R, K58M, N61G, N61T, D62I, D62R, D62Q, D62L, D62S, D62V, D62N, D62K, H103D, H103G, H107M, G109A and Y112D. Further, in some embodiments, the antibody may comprise two or more substitutions selected from Q1E, S30R, N32D, N32E, S33G, S37N, G44S, I53T, K55Y, S57K, S57R, K58M, N61G, N61T, D62I, D62R, D62Q, D62L, D62S, D62V, D62N, D62K, H103D, H103G, H107M, G109A and Y112D.

In some embodiments, the heavy chain of 4B7 has the following substitutions relative to SEQ ID NO:3:
N32D+D62Q+H107M+Y112D; N32D+D62R+H103D+H107M+Y112D; N32D+D62R+H107M+Y112D; N32D+D62R+Y112D; D62Q+Y112D; D62R+Y112D; D62R+H107M+Y112D; N32D+D62Q+Y112D; N32D+D62R+H107M; N32D+D62S+H107M+Y112D; D62Q+H107M+Y112D; N32D+D62R+H103D; D62S+H107M+Y112D; S30R+S57K; N61G+D62V; and K58M+D62N. In some embodiments, the heavy chain of 4B7 has the following substitutions relative to SEQ ID NO:3: D62Q+H107M+Y112D; D62Q+Y112D; D62R+H107M+Y112D; D62R+Y112D; D62S+H107M+Y112D; N32D+D62K+Y112D; N32D+D62Q+H107M+Y112D; N32D+D62Q+Y112D; N32D+D62R+H103D; N32D+D62R+H103D+H107M+Y112D; N32D+D62R+H107M; N32D+D62R+H107M+Y112D; N32D+D62R+Y112D; N32D+D62S+H107M+Y112D; N32D+G44S+D62R+Y112D; N32D+I53T+D62Q+Y112D; N32D+I53T+D62R+Y112D; N32D+K55Y+D62Q+Y112D; N32D+K55Y+D62R+Y112D; N32D+S37N+D62R+Y112D; Q1E+N32D+D62R+Y112D; Q1E+N32D+G44S+K55Y+D62R+Y112D; N32D+G44S+K55Y+D62R+Y112D; S30R+S57K; N61G+D62V; and K58M+D62N.

Further, provided is an isolated monoclonal antibody that binds to human tissue factor pathway inhibitor, wherein the antibody comprises an amino acid sequence shown in SEQ ID NO:4 comprising one or more amino acid modifications. In some embodiments, the modification of the light chain of 4B7 is selected from a substitution, an insertion or a deletion.

In some embodiments, the substitutions are located in the CDRs of the light chain of 4B7. In other embodiments, the substitutions are located outside the CDRs of the light chain of 4B7.

In some embodiments, the substitution of the light chain of 4B7 is at a position selected from F31, S32, D33, N35, Y37, Y54, G56, S57, S61 and D97. In some embodiments, the substitution of the light chain of 4B7 may also include a position selected from M4, V30, T36, N39, L42, K44, Q50, L51, K55, A60 and S98. For example, the substitution may be selected from M4I, M4L, V30L, F31I, F31M, F31Y, F31H, S32L, S32R, S32Y, D33F, D33R, N35I, N35L, N35T, N35V, T36N, Y37F, N39D, L42Q, K44R, Q50R, L51R, Y54F, K55L, G56D, G56A, G56V, S57Y, A60D, S61C, D97M, D97T and S98H. Further, in some embodiments, the antibody may comprise two or more substitutions selected from M4I, M4L, V30L, F31I, F31M, F31Y, S32L, S32R, S32Y, D33F, D33R, N35I, N35L, N35T, N35V, T36N, Y37F, N39D, L42Q, K44R, Q50R, Y54F, K55L, G56D, G56A, G56V, S57Y, A60D, S61C, D97M, D97T and S98H.

In some embodiments, the light chain of 4B7 has the following substitutions relative to SEQ ID NO:4: S32R+N35T; S32R+N35T+D97T; S32R+D33F+N35I; S32R+D33F+N35I+D97T; S32R+D33F+N35T; S32R+D33F; S32R+D33R+N35I; S32R+D33R+N35I+D97T; S32R+D33R; S32R+D33R+N35T; N35T+D97T; D33F+N35I; D33F+N35I+D97T; D33F+N35T+Y37F; D33R+N35I; D33R+N35I+D97T; D33R+N35T; F31I+S32R+N35I+D97T; F31I+S32R+D33F+N35I+D97T; F31I+S32R+D33F+N35T; F31I+S32R+D33R+N35I+D97T; F31I+N35I; F31I+D33F+N35I; F31I+D33F+N35I+D97T; F31I+D33R+N35I; F31I+D33R; F31M+S32L+D33R+N35I+D97T; F31M+S32R+D33F+N35I; F31M+S32R+D33F+N35I+D97T; F31M+S32R+D33F+D97T; F31M+S32R+D33R+N35I; F31M+S32R+D33R+N35I+D97T; F31M+S32R+D33R; F31M+S32R+D33R+N35T; F31M+D33F+N35I; F31M+D33F; F31M+D33F+N35T; F31M+D33R+N35I; F31M+D33R; S32R+N35I; F31M+D33F+N35T+Y37F; N35V+G56D; N35L+G56A; and D33F+Y54F.

In some embodiments, the light chain of 4B7 has the following substitutions relative to SEQ ID NO:4: D33F+N35I; D33F+N35I+D97T; D33F+N35T+Y37F; D33R+N35I; D33R+N35I+D97T; D33R+N35T; F31H+S32R+D33F+N35I+D97T; F31I+D33F+N35I; F31I+D33F+N35I+D97T; F31I+D33F+N35I+K44R; F31I+D33F+N35I+L42Q; F31I+D33F+N35I+S98H; F31I+D33F+N35I+T36N; F31I+D33R; F31I+D33R+N35I; F31I+N35I; F31I+S32R+D33F+N35I+D97T; F31I+S32R+D33F+N35T; F31I+S32R+D33R+N35I+D97T; F31I+S32R+N35I+D97T; F31M+D33F; F31M+D33F+N35I; F31M+D33F+N35T; F31M+D33F+N35T+Y37F; F31M+D33R; F31M+D33R+N35I; F31M+S32L+D33R+N35I+D97T; F31M+S32R+D33F+D97T; F31M+S32R+D33F+N35I; F31M+S32R+D33F+N35I+D97T; F31M+S32R+D33R; F31M+S32R+D33R+N35I; F31M+S32R+D33R+N35I+D97T; F31M+S32R+D33R+N35T; F31Y+S32R+D33F+N35I+D97T; M4I+S32R+D33F+N35I+D97T; M4L+S32R+D33F+N35I+D97T; N35T+D97T; S32R+D33F; S32R+D33F+N35I; S32R+D33F+N35I+A60D+D97T; S32R+D33F+N35I+D97T; S32R+D33F+N35I+D97T+S98H; S32R+D33F+N35I+G56V+D97T; S32R+D33F+N35I+K44R+D97T; S32R+D33F+N35I+K55L+D97T; S32R+D33F+N35I+L42Q+D97T; S32R+D33F+N35I+L51R+D97T; S32R+D33F+N35I+N39D+D97T; S32R+D33F+N35I+Q50R+D97T; S32R+D33F+N35I+T36N+D97T; S32R+D33F+N35T; S32R+D33R; S32R+D33R+N35I; S32R+D33R+N35I+D97T; S32R+D33R+N35T; S32R+N35I; S32R+N35T; S32R+N35T+D97T; V30L+F31I+D33F+N35I; V30L+S32R+D33F+N35I+D97T; V30L+S32R+D33F+N35I+T36N+D97T; V30L+S32R+N35I+T36N; N35V+G56D; N35L+G56A; and D33F+Y54F.

Also provided is an isolated monoclonal antibody that binds to human tissue factor pathway inhibitor, wherein the antibody comprises: a) a heavy chain comprising an amino acid sequence shown in SEQ ID NO:3, wherein said heavy chain amino acid sequence comprises one or more amino acid modifications; and b) a light chain comprising an amino acid sequence shown in SEQ ID NO:4, wherein said light chain amino acid sequence comprises one or more amino acid modifications. Examples of modifications that can be made are provided above.

In some embodiments, the isolated monoclonal antibody that binds to human tissue factor pathway inhibitor comprises a heavy chain comprising an amino acid sequence selected from SEQ ID NO: 19, 20, 21, 22, 23, 24, 25 and 26.

In some embodiments, the isolated monoclonal antibody that binds to human tissue factor pathway inhibitor comprises a light chain comprising an amino acid sequence selected from SEQ ID NO: 27, 28, 29, 30, 31, 32, 33 and 34.

In some embodiments, the isolated monoclonal antibody that binds to human tissue factor pathway inhibitor comprises: a) a heavy chain comprising an amino acid sequence selected from SEQ ID NO: 19, 20, 21, 22, 23, 24, 25 and 26; and b) a light chain comprising an amino acid sequence selected from SEQ ID NO: 27, 28, 29, 30, 31, 32, 33 and 34. In some embodiments, the isolated monoclonal antibody that binds to human tissue factor pathway inhibitor comprises: a) a heavy chain comprising an amino acid sequence shown in SEQ ID NO: 19; and b) a light chain comprising an amino acid sequence shown in SEQ ID NO: 27. In some embodiments, the isolated monoclonal antibody that binds to human tissue factor pathway inhibitor comprises: a) a heavy chain comprising an amino acid sequence shown in SEQ ID NO: 20; and b) a light chain comprising an amino acid sequence shown in SEQ ID NO: 28. In some embodiments, the isolated monoclonal antibody that binds to human tissue factor pathway inhibitor comprises: a) a heavy chain comprising an amino acid sequence shown in SEQ ID NO: 21; and b) a light chain comprising an amino acid sequence shown in SEQ ID NO: 29. In some embodiments, the isolated monoclonal antibody that binds to human tissue factor pathway inhibitor comprises: a) a heavy chain comprising an amino acid sequence shown in SEQ ID NO: 22; and b) a light chain comprising an amino acid sequence shown in SEQ ID NO: 30. In some embodiments, the isolated monoclonal antibody that binds to human tissue factor pathway inhibitor comprises: a) a heavy chain comprising an amino acid sequence shown in SEQ ID NO: 23; and b) a light chain comprising an amino acid sequence shown in SEQ ID NO: 31. In some embodiments, the isolated monoclonal antibody that binds to human tissue factor pathway inhibitor comprises: a) a heavy chain comprising an amino acid sequence shown in SEQ ID NO: 24; and b) a light chain comprising an amino acid sequence shown in SEQ ID NO: 32. In some embodiments, the isolated monoclonal antibody that binds to human tissue factor pathway inhibitor comprises: a) a heavy chain comprising an amino acid sequence shown in SEQ ID NO: 25; and b) a light chain comprising an amino acid sequence shown in SEQ ID NO: 33. In some embodiments, the isolated monoclonal antibody that binds to human tissue factor pathway inhibitor comprises: a) a heavy chain comprising an amino acid sequence shown in SEQ ID NO: 26; and b) a light chain comprising an amino acid sequence shown in SEQ ID NO: 34.

2A8/4B7 Variant Combinations

It is also contemplated that the isolated monoclonal antibody that binds to human tissue factor pathway inhibitor may comprise combinations of the heavy and light chains of 2A8 and 4B7.

Accordingly, provided is an isolated monoclonal antibody that binds to human tissue factor pathway inhibitor, wherein the antibody comprises: a) a heavy chain of 2A8 comprising an amino acid sequence shown in SEQ ID NO:1, wherein said heavy chain amino acid sequence comprises one or more amino acid modifications; and b) a light chain of 4B7 comprising an amino acid sequence shown in SEQ ID NO:4, wherein said light chain amino acid sequence comprises one or more amino acid modifications. Examples of modifications that can be made are provided above.

Also provided is an isolated monoclonal antibody that binds to human tissue factor pathway inhibitor, wherein the antibody comprises: a) a heavy chain of 4B7 comprising an amino acid sequence shown in SEQ ID NO:3, wherein said heavy chain amino acid sequence comprises one or more amino acid modifications; and b) a light chain of 2A8 comprising an amino acid sequence shown in SEQ ID NO:2, wherein said light chain amino acid sequence comprises one or more amino acid modifications. Examples of modifications that can be made are provided above.

In some embodiments, provided is an isolated monoclonal antibody that binds to human tissue factor pathway inhibitor, wherein the antibody comprises: a) a heavy chain comprising an amino acid sequence selected from the group consisting of SEQ ID NO:5, 6, 7, 8, 9, 10, 11, 19, 20, 21, 22, 23, 24, 25, and 26; and b) a light chain comprising an amino acid sequence selected from the group consisting of SEQ ID NO:12, 13, 14, 15, 16, 17, 18, 27, 28, 29, 30, 31, 32, 33, and 34.

Nucleic Acids, Vectors and Host Cells

Also provided are isolated nucleic acid molecules encoding any of the monoclonal antibodies described above.

Thus, provided is an isolated nucleic acid molecule encoding an antibody that binds to human tissue factor pathway inhibitor, wherein the antibody comprises a heavy chain comprising an amino acid sequence shown in SEQ ID NO:1, wherein said heavy chain amino acid sequence comprises one or more amino acid modifications. Examples of such modifications are described above.

Also provided is an isolated nucleic acid molecule encoding an antibody that binds to human tissue factor pathway inhibitor, wherein the antibody comprises a light chain comprising an amino acid sequence shown in SEQ ID NO:2, wherein said light chain amino acid sequence comprises one or more amino acid modifications. Examples of such modifications are described above.

Also provided is an isolated nucleic acid molecule encoding an antibody that binds to human tissue factor pathway inhibitor, wherein the antibody comprises a heavy chain comprising an amino acid sequence shown in SEQ ID NO:3, wherein said heavy chain amino acid sequence comprises one or more amino acid modifications. Examples of such modifications are described above.

Also provided is an isolated nucleic acid molecule encoding an antibody that binds to human tissue factor pathway inhibitor, wherein the antibody comprises a light chain comprising an amino acid sequence shown in SEQ ID NO:4, wherein said light chain amino acid sequence comprises one or more amino acid modifications. Examples of such modifications are described above.

Further, also provided are vectors comprising the isolated nucleic acid molecules encoding any of the monoclonal antibodies described above and host cells comprising such vectors.

Methods of Preparing Antibodies to TFPI

The monoclonal antibody may be produced recombinantly by expressing a nucleotide sequence encoding the variable regions of the monoclonal antibody according to the embodiments of the invention in a host cell. With the aid of an expression vector, a nucleic acid containing the nucleotide sequence may be transfected and expressed in a host cell suitable for the production. Accordingly, also provided is a method for producing a monoclonal antibody that binds with human TFPI comprising:

(a) transfecting a nucleic acid molecule encoding a monoclonal antibody of the invention into a host cell, (b) culturing the host cell so to express the monoclonal antibody in the host cell, and optionally (c) isolating and purifying the produced monoclonal antibody, wherein the nucleic acid molecule comprises a nucleotide sequence encoding a monoclonal antibody of the present invention.

In one example, to express the antibodies, or antibody fragments thereof, DNAs encoding partial or full-length light and heavy chains obtained by standard molecular biology techniques are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain encoding genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Examples of selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Examples of mammalian host cells for expressing the recombinant antibodies include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells, HKB11 cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods, such as ultrafiltration, size exclusion chromatography, ion exchange chromatography and centrifugation.

Use of Partial Antibody Sequences to Express Intact Antibodies

Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. Sci. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. It is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts are used to design an overlapping set of synthetic oligonucleotides to create synthetic V sequences with identical amino acid coding capacities as the natural sequences. The synthetic heavy and light chain sequences can differ from the natural sequences. For example: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and restriction sites are engineered upstream or downstream of the translation initiation sites.

For both the heavy and light chain variable regions, the optimized coding, and corresponding non-coding, strand sequences are broken down into 30-50 nucleotide sections at approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains.

Thus, in another aspect, the structural features of a human anti-TFPI antibody are used to create structurally related human anti-TFPI antibodies that retain the function of binding to TFPI. More specifically, one or more CDRs of the specifically identified heavy and light chain regions of the monoclonal antibodies of the invention can be combined recombinantly with known human framework regions and CDRs to create additional, recombinantly-engineered, human anti-TFPI antibodies of the invention.

Pharmaceutical Compositions

Also provided are pharmaceutical compositions comprising therapeutically effective amounts of anti-TFPI monoclonal antibody and a pharmaceutically acceptable carrier. "Pharmaceutically acceptable carrier" is a substance that may be added to the active ingredient to help formulate or stabilize the preparation and causes no significant adverse toxicological effects to the patient. Examples of such carriers are well known to those skilled in the art and include water, sugars such as maltose or sucrose, albumin, salts such as sodium chloride, etc. Other carriers are described for example in Remington's Pharmaceutical Sciences by E. W. Martin. Such compositions will contain a therapeutically effective amount of at least one anti-TFPI monoclonal antibody.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. The composition is preferably formulated for parenteral injection. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In some cases, it will include isotonic agents, for example, sugars, polyalcohols such as mannitol, sorbitol, or sodium chloride in the composition.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

Pharmaceutical Uses

The monoclonal antibody can be used for therapeutic purposes for treating genetic and acquired deficiencies or defects in coagulation. For example, the monoclonal antibodies in the embodiments described above may be used to block the interaction of TFPI with FXa, or to prevent TFPI-dependent inhibition of the TF/FVIIa activity. Additionally, the monoclonal antibody may also be used to restore the TF/FVIIa-driven generation of FXa to bypass the insufficiency of FVIII- or FIX-dependent amplification of FXa.

The monoclonal antibodies have therapeutic use in the treatment of disorders of hemostasis such as thrombocytopenia, platelet disorders and bleeding disorders (e.g., hemophilia A, hemophilia B and hemophlia C). Such disorders may be treated by administering a therapeutically effective amount of the anti-TFPI monoclonal antibody to a patient in need thereof. The monoclonal antibodies also have therapeutic use in the treatment of uncontrolled bleeds in indications such as trauma and hemorrhagic stroke. Thus, also provided is a method for shortening the bleeding time comprising administering a therapeutically effective amount of an anti-TFPI monoclonal antibody of the invention to a patient in need thereof.

The antibodies can be used as monotherapy or in combination with other therapies to address a hemostatic disorder. For example, co-administration of one or more antibodies of the invention with a clotting factor such as factor VIIa, factor VIII or factor IX is believed useful for treating hemophilia. In one embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defects. In another embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defects, and further wherein factor VII is not coadministered. The invention also includes a pharmaceutical composition comprising a therapeutically effective amount of the combination of a monoclonal antibody of the invention and factor VIII or factor IX, wherein the composition does not contain factor VII. "Factor VII" includes factor VII and factor VIIa. These combination therapies are likely to reduce the necessary infusion frequency of the clotting factor. By co-administration or combination therapy is meant administration of the two therapeutic drugs each formulated separately or formulated together in one composition, and, when formulated separately, administered either at approximately the same time or at different times, but over the same therapeutic period.

In some embodiments, one or more antibodies described herein can be used in combination to address a hemostatic disorder. For example, co-administration of two or more of the antibodies described herein is believed useful for treating hemophilia or other hemostatic disorder.

The pharmaceutical compositions may be parenterally administered to subjects suffering from hemophilia A or B at a dosage and frequency that may vary with the severity of the bleeding episode or, in the case of prophylactic therapy, may vary with the severity of the patient's clotting deficiency.

The compositions may be administered to patients in need as a bolus or by continuous infusion. For example, a bolus administration of an inventive antibody present as a Fab fragment may be in an amount of from 0.0025 to 100 mg/kg body weight, 0.025 to 0.25 mg/kg, 0.010 to 0.10 mg/kg or 0.10-0.50 mg/kg. For continuous infusion, an inventive antibody present as an Fab fragment may be administered at 0.001 to 100 mg/kg body weight/minute, 0.0125 to 1.25 mg/kg/min., 0.010 to 0.75 mg/kg/min., 0.010 to 1.0 mg/kg/min. or 0.10-0.50 mg/kg/min. for a period of 1-24 hours, 1-12 hours, 2-12 hours, 6-12 hours, 2-8 hours, or 1-2 hours. For administration of an inventive antibody present as a full-length antibody (with full constant regions), dosage amounts may be about 1-10 mg/kg body weight, 2-8 mg/kg, or 5-6 mg/kg. Such full-length antibodies would typically be administered by infusion extending for a period of thirty minutes to three hours. The frequency of the administration would depend upon the severity of the condition. Frequency could range from three times per week to once every two weeks to six months.

Additionally, the compositions may be administered to patients via subcutaneous injection. For example, a dose of 10 to 100 mg anti-TFPI antibody can be administered to patients via subcutaneous injection weekly, biweekly or monthly.

As used herein, "therapeutically effective amount" means an amount of an anti-TFPI monoclonal antibody or of a combination of such antibody and factor VIII or factor IX that is needed to effectively increase the clotting time in vivo or otherwise cause a measurable benefit in vivo to a patient in need. The precise amount will depend upon numerous factors, including, but not limited to the components and physical characteristics of the therapeutic composition, intended patient population, individual patient considerations, and the like, and can readily be determined by one skilled in the art.

EXAMPLES

Example 1

Cloning, Expression and Quantification of Antibody Expression Levels

The heavy and light chain of the wild-type Fabs 2A8 and 4B7 carrying a c-myc-tag and a hexa-histidine tag at the C-terminus of the heavy chain were subcloned into the pET28a bacterial expression vector (Novagen/Merck Chemicals Ltd., Nottingham, UK) and transformed into Top10F' cells (Invitrogen GmbH, Karlsruhe, Germany). Alternatively, other bacterial expression vectors (e.g. pQE vector system, Qiagen GmbH, Hilden, Germany) and strains (e.g. DH5α, Invitrogen GmbH, Karlsruhe, Germany) can be used. Variants were generated by standard oligo-based site-directed mutagenesis and confirmed by DNA sequencing. In particular, amino acid residues within or surrounding complementary determining regions were modified within the heavy and/or the light chain.

To be able to use wild-type or mutant antibodies as competitors, epitope-tags located at the C-terminus of the heavy chain were either removed or replaced using standard PCR-based techniques. In particular, for 4B7 the c-myc-tag was exchanged to a haemagglutinin (HA) epitope tag for all variants analyzed. In contrast, 4B7 wild-type or variants used as competitors carried a c-myc-tag. In case of 2A8, the c-myc-epitope tag was either replaced by a HA-tag or deleted, resulting in a variant that only displayed a 6×Histidine epitope tag at its C-terminus.

For expression, variants were transformed into the BL21starDE3 *Escherichia coli* strain (Invitrogen, C6010-03), inoculated into an overnight culture in LB medium containing kanamycin (30 µg/ml) and incubated at 37° C. for 18 hours. Expression cultures were generated by inoculating the overnight culture 1:20 into fresh LB medium with kanamycin (30 µg/ml). After 6 hours, 1 mM isopropyl-b-D-1-thiogalactopyranoside (Roth, 2316.5) was added to induce antibody expression and the cultures were incubated for additional 18 hours at 30° C. Alternatively, overnight cultures were inoculated 1:20 into the autoinduction medium Overnight Express TB medium (Merck, 71491) and incubated at 30° C. for 24 hours.

For quantification of expression levels an ELISA approach was used. Briefly, MTP plates (Nunc maxisorp black, 460518) were incubated with a Fab-specific antibody (Sigma, I5260) diluted in coating buffer (Candor Bioscience GmbH, 121500) at 4° C. over night, washed with PBST (phosphate buffered saline: 137 mM NaCl, Merck 1.06404.5000; 2.7 mM KCl, Merck 1.04936.1000; 10 mM $Na_2HPO_4$, Merck 1.06586.2500, 1.8 mM $KH_2PO_4$, Merck 1.04871.5000; containing 0.05% Tween 20 Acros Organics, 233360010), blocked with 2% milk in PBST for 1 h at room temperature and washed again. Cultures were diluted in 0.25% skim milk (Fluka analytical, 70166) in PBS and bound to the MTP plates for 1 h at room temperature. After washing with PBST, captured antibodies were incubated with a HRP-coupled anti-Fab antibody (Sigma, A0293) and detected by incubating the plate with 10 µM amplex red substrate (Invitrogen, A12222) for 10 to 30 minutes at room temperature in the dark followed by fluorescence measurement. Expression levels were normalized after determining the concentration relative to the wild-type purified antibody (2A8 or 4B7).

Example 2

Determination of Activity and Interspecies Cross Reactivity of Generated Antibody Variants To determine the activity of the mutated antibody variants on human or mouse TFPI (American Diagnostica, 4900B and R&D Systems, 2975-P1, respectively) an equilibrium or competitive ELISA assay format was used. Briefly, MTP plates (either Mesoscale Discovery, L21XA-4 or Nunc maxisorp black, 460518) were coated with 0.04-2 μg/ml either human or mouse TFPI diluted in phosphate buffered saline (PBS) or in coating buffer (Candor Bioscience GmbH, 121500), respectively and incubated over night at 4° C. After washing, plates were blocked with 3% bovine serum albumin (Sigma, A4503) in PBST for 1 hour at room temperature and the washing step was repeated. For binding of the antibodies 10-25 μl of culturing supernatants normalized to their respective antibody expression level (if not otherwise indicated) were added to the plates for 1 hour at RT followed by washing with PBST. Bound wild-type and variants were then either detected by an epitope tag specific antibody or a competition step was included. For competition, 50-300 nM competitor or free antigen was added and incubated for 20 minutes to 24 hours at room temperature. After washing, the remaining variants were detected with an epitope tag specific antibody either coupled to horseradish peroxidase (Biomol, anti-c-myc A190-105P for 2A8 variants and anti-HA A190-108P for 4B7 variants) or by an anti-myc (Sigma, C3956) or anti-HA antibody (Sigma, H6908) which was previously labeled with a sulfo-NHS reagent according to the manufacturer's instructions for electrochemiluminiscent detection (Mesoscale Discovery, R91AN-1). For signal detection in maxisorp plates 10 μM amplex red substrate (Invitrogen, A12222) was added and incubated for 10 to 30 minutes at room temperature in the dark followed by fluorescence measurement. For the detection in MSD plates MSD read buffer T was diluted to 2× in $H_2O$ (Mesoscale Discovery, R92TC-1), added to the plates and the electrochemiluminiscence signal was detected at 620 nm using the Mesoscale Discovery Sector Imager 6000.

Example 3

Single and Multiple Amino Acid Substitutions

Provided in Table 1 are several examples of single amino acid substitutions introduced into the heavy or light chain of 2A8. The expression level of the variants was analyzed in quadruples in the quantification ELISA. After normalization to the respective expression level, performance was analyzed in quadruples in the competitive ELISA on human and murine TFPI and variant to wild-type (wt) ratios were determined. Errors were calculated by error propagation from the standard deviations.

TABLE 1

Analysis of single amino acid substitutions within 2A8.

| | hTFPI | | mTFPI | |
|---|---|---|---|---|
| 2A8 variants | variant/wild-type | error | variant/wild-type | error |
| HC_S31P | 3.6 | 0.5 | 2.4 | 0.3 |
| HC_S31V | 9.7 | 1.1 | 7.4 | 4.1 |
| HC_G33K | 1.8 | 0.2 | 0.7 | 0.1 |
| HC_G33P | 5.1 | 0.6 | 2.9 | 0.4 |
| HC_S35L | 1.7 | 0.1 | 1.5 | 0.2 |
| HC_S35D | 4.3 | 0.6 | 2.6 | 0.6 |
| HC_I51D | 3.9 | 0.3 | 1.4 | 0.2 |
| HC_I51E | 7.3 | 0.6 | 0.7 | 0.1 |
| HC_S54F | 6.5 | 0.6 | 3.1 | 0.6 |
| HC_S54D | 1.7 | 0.2 | 1.2 | 0.2 |
| HC_S55A | 2.0 | 0.3 | 1.2 | 0.2 |
| HC_S55R | 4.4 | 1.1 | 2.1 | 0.3 |
| HC_K99V | 7.5 | 0.9 | 3.9 | 0.5 |
| HC_K99L | 13.5 | 1.4 | 10.8 | 2.8 |
| HC_F104Y | 2.0 | 0.3 | 1.5 | 0.2 |
| LC_A32N | 3.5 | 0.4 | 2.0 | 0.3 |
| LC_Y48F | 4.6 | 0.6 | 3.2 | 0.7 |
| LC_N51V | 4.4 | 0.4 | 2.0 | 0.4 |
| LC_N52G | 3.4 | 0.5 | 1.5 | 0.2 |
| LC_P54L | 5.3 | 0.8 | 2.7 | 0.5 |
| LC_D91L | 4.2 | 0.3 | 1.6 | 0.5 |
| LC_D91R | 3.1 | 0.5 | 2.0 | 0.3 |
| LC_D91W | 7.4 | 0.7 | 4.0 | 0.7 |
| LC_D91K | 3.5 | 0.4 | 1.4 | 0.2 |
| LC_D92S | 3.8 | 0.5 | 2.6 | 0.3 |
| LC_D92T | 2.6 | 0.4 | 1.2 | 0.2 |
| LC_V96G | 3.2 | 0.4 | 1.2 | 0.2 |
| LC_V96M | 3.5 | 0.5 | 1.5 | 0.2 |
| LC_V96W | 4.0 | 0.4 | 4.3 | 0.6 |
| HC_S31P | 3.6 | 0.5 | 2.4 | 0.3 |
| HC_S31V | 9.7 | 1.1 | 7.4 | 4.1 |
| HC_G33K | 1.8 | 0.2 | 0.7 | 0.1 |
| HC_G33P | 5.1 | 0.6 | 2.9 | 0.4 |
| HC_S35L | 1.7 | 0.1 | 1.5 | 0.2 |
| HC_S35D | 4.3 | 0.6 | 2.6 | 0.6 |
| HC_I51D | 3.9 | 0.3 | 1.4 | 0.2 |
| HC_I51E | 7.3 | 0.6 | 0.7 | 0.1 |
| HC_S54F | 6.5 | 0.6 | 3.1 | 0.6 |
| HC_S54D | 1.7 | 0.2 | 1.2 | 0.2 |
| HC_S55A | 2.0 | 0.3 | 1.2 | 0.2 |
| HC_S55R | 4.4 | 1.1 | 2.1 | 0.3 |
| HC_K99V | 7.5 | 0.9 | 3.9 | 0.5 |
| HC_K99L | 13.5 | 1.4 | 10.8 | 2.8 |
| HC_F104Y | 2.0 | 0.3 | 1.5 | 0.2 |
| LC_A32N | 3.5 | 0.4 | 2.0 | 0.3 |
| LC_Y48F | 4.6 | 0.6 | 3.2 | 0.7 |
| LC_N51V | 4.4 | 0.4 | 2.0 | 0.4 |
| LC_N52G | 3.4 | 0.5 | 1.5 | 0.2 |
| LC_P54L | 5.3 | 0.8 | 2.7 | 0.5 |
| LC_D91L | 4.2 | 0.3 | 1.6 | 0.5 |
| LC_D91R | 3.1 | 0.5 | 2.0 | 0.3 |
| LC_D91W | 7.4 | 0.7 | 4.0 | 0.7 |
| LC_D91K | 3.5 | 0.4 | 1.4 | 0.2 |
| LC_D92S | 3.8 | 0.5 | 2.6 | 0.3 |
| LC_D92T | 2.6 | 0.4 | 1.2 | 0.2 |
| LC_V96G | 3.2 | 0.4 | 1.2 | 0.2 |
| LC_V96M | 3.5 | 0.5 | 1.5 | 0.2 |
| LC_V96W | 4.0 | 0.4 | 4.3 | 0.6 |

Provided in Table 2 are some examples of combined amino acid substitutions within 2A8 TFPI antibodies. While not every combination is provided in Table 2, it is contemplated that the TFPI antibody may comprise any combination of modifications provided. The expression level of variants was analyzed in quadruples in the quantification ELISA. If not otherwise indicated, variants were normalized to the respective expression level and performance was analyzed in quadruples in the competitive ELISA on human and murine TFPI followed by calculation of variant to reference (HC_K99L) ratios. Values are marked with "#" in case variant performance was analyzed without prior normalization and variant to reference ratios were normalized to the expression level by dividing the assay signal by the expression level. In cases were a different reference was used in the competitive ELISA and variants were analyzed without prior normalization, values are marked with "*". For these variants, the value listed in the table was calculated by multiplying the ratios variant/alternative reference with alternative reference/HC_K99L. Errors were calculated by error propagation from the standard deviations.

TABLE 2

Example of multiple amino acid substitutions within 2A8.

| 2A8 HC | | | | | | | | | | | | | 2A8 LC | | | | | | | | |
|---|---|---|---|---|---|---|---|---|---|---|---|---|---|---|---|---|---|---|---|---|---|
| Q1 | R30 | S31 | G33 | M34 | S35 | S50 | I51 | R52 | S54 | S55 | S56 | K99 | D1 | I2 | A13 | S21 | N26 | R28 | N29 | H33 | Y48 |
| | | V | | | | | D | | F | | | V | | | | | | | | | F |
| | | | P | | D | | | | F | | | L | | | | | | | | | F |
| | | | | | D | | D | | | R | | V | | | | | | | | | F |
| | | | | | L | | | | F | | | V | | | | | | | | | F |
| | | V | P | | D | | | | | | | | | | | | | | | | F |
| | | | | | D | | D | | | | | L | | | | | | | | | F |
| | | V | | | | | D | | | R | | L | | | | | | | | | F |
| | | V | | | D | | D | | | | | V | | | | | | | | | F |
| | | | P | | | | D | | F | | | | | | | | | | | | F |
| | | | | | | | D | | F | | | L | | | | | | | | | |
| | | V | | | D | | | | F | | | | | | | | | | | | F |
| | | | | | D | | | | | | | L | | | | | | | | | |
| | | V | P | | | | D | | F | | | V | | | | | | | | | F |
| | | | | | D | | E | | | R | | L | | | | | | | | | F |
| | | V | | | | | | | | | | V | | | | | | | | | |
| | | V | | | | | E | | | R | | V | | | | | | | | | F |
| | | | | | D | | | | | | | L | | | | | | | | | F |
| | | V | | | | | | | F | | | L | | | | | | | | | |
| | | V | P | | D | | | | | | | | | | | | | | | | F |
| | | | | | D | | | | | R | | L | | | | | | | | | F |
| | | V | | | D | | | | | R | | | | | | | | | | | F |
| | | V | | | D | | | | | | | | | | | | | | | | F |
| | | V | | | | | D | | | R | | | | | | | | | | | F |
| | | | | | D | | | | F | R | | L | | | | | | | | | |
| | | V | | | L | | D | | F | | | V | | | | | | | | | |
| | | V | | | L | | E | | F | | | V | | | | | | | | | |
| | | | | | D | | | | | | | L | | | | | | | | | |
| | | | | | D | | | | | | | L | | | | | | | | | F |
| | | V | | | | | D | | | R | | V | | | | | | | | | F |
| | | | | | D | | | | | R | | L | | | | | | | | | F |
| | | | | | D | | | | | R | | L | S | | | | | | | | F |
| | | | | | D | | | | | R | | L | | Y | | | | | | | F |
| | | | | | D | | | | | R | | L | | | S | | | | | | F |
| | | | | | D | | | | | R | | L | | | | T | | | | | F |
| | | | | | D | | | | | R | | L | | | | | A | | | | F |
| | | | | | D | | | | | R | | L | | | | | | P | | | F |
| | | | | | D | | | | | R | | L | | | | | | | K | | F |
| | | | | | D | | | | | R | | L | | | | | | | | Y | F |
| | | | | | D | | | | | R | | L | | | | | | | | | F |
| | | | | | D | | | | | R | | L | | | | | | | | | F |
| | | | | | D | | | | | R | | L | | | | | | | | | F |
| | | | | | D | | | | | R | | L | | | | | | | | | F |
| | | | | | D | | | | | R | | L | | | | | | | | | F |
| | | | | | D | | | | | R | | L | | | | | | | | | F |
| | | | | | D | | | | | R | | L | | | | | | | | | F |
| E | | | | | D | | | | | R | | L | | | | | | | | | F |
| | S | | | | D | | | | | R | | L | | | | | | | | | F |
| | | | A | | D | | | | | R | | L | | | | | | | | | F |
| | | | | I | D | | | | | R | | L | | | | | | | | | F |
| | | | | K | D | | | | | R | | L | | | | | | | | | F |
| | | | | | D | A | | | | R | | L | | | | | | | | | F |
| | | | | | D | | | S | | R | | L | | | | | | | | | F |
| | | | | | D | | | | | R | G | L | | | | | | | | | F |
| E | S | | | | D | | | | | R | G | L | S | Y | S | T | | P | K | | F |
| E | S | | | | D | | | | | R | G | L | | | | | | | | | F |
| | | | | | D | | | | | R | | L | S | Y | S | T | | P | K | | F |
| E | S | | | | D | | | | | R | G | L | S | Y | S | T | | P | | | F |
| E | S | | | | D | | | | | R | G | L | S | Y | S | T | | P | K | | F |
| E | S | | | | D | | | | | R | G | L | S | Y | S | T | | P | | | F |
| | | | | | D | | | | | | | L | | | | | | | | | F |
| | | | | | D | | | | | | | L | | | | | | | | | F |
| | | | | | D | | | | | | | L | | | | | | | | | F |
| | | | | | D | | | | | | | L | | | | | | | | | F |
| | | | | | D | | | | | | | L | | | | | | | | | F |
| | | | | | D | | | | | | | L | | | | | | | | | F |
| | | | | | D | A | | | | | | L | | | | | | | | | F |
| | | | | | D | | | S | | | | L | | | | | | | | | F |

TABLE 2-continued

Example of multiple amino acid substitutions within 2A8.

| | | | | | | | | | | | | | | |
|---|---|---|---|---|---|---|---|---|---|---|---|---|---|---|
| | | | | | D | | | G | | L | | | | F |
| | | | | | D | | G | | L | | | | | F |
| E | S | | | | D | | G | G | | L | | | | F |
| | S | V | | | | D | | R | | V | | | | F |
| | | V | A | | | D | | R | | V | | | | F |
| | | V | | A | D | | | R | | V | | | | F |
| | | V | | | D | S | | R | | V | | | | F |
| | | V | | | D | | | R | G | V | | | | F |
| E | | V | | A | D | | | R | G | V | | | | F |
| | | V | | | D | | | R | | V | S | Y | S | T | P | K | F |
| E | | V | | A | D | | | R | G | V | S | Y | S | T | P | K | F |
| E | | V | | A | D | | | R | G | V | S | Y | S | T | P | K | F |
| | | V | | | D | | | R | | V | S | Y | S | T | P | K | F |
| | | V | | | D | | | R | | V | S | Y | S | T | P | K | F |

| | | | | | | | | | | | | 2A8 LC | | | | | | | hTFPI | | mTFPI | |
|---|---|---|---|---|---|---|---|---|---|---|---|---|---|---|---|
| Y49 | N51 | N52 | G56 | E80 | S89 | D91 | D92 | G93 | V94 | P95 | V96 | variant/HC_K99L | error | variant/HC_K99L | error |
| V | | | | | | | | | | | | 8.1# | 0.4 | 2.2# | 0.4 |
| | G | | | | | | | | | | | 6.2# | 1.4 | 2.3# | 0.8 |
| V | | | | | | | | | | | | 8.0# | 0.5 | 2.7# | 0.4 |
| | | | | | | K | | | | | | 5.0# | 0.6 | 3.1# | 0.5 |
| | | | | | | L | | | | W | | 22.5# | 1.6 | 5.9# | 1.3 |
| | | | | | | W | | | | | | 0.8# | 0.1 | 0.2# | 0.0 |
| | G | | | | | L | | | | W | | 0.4# | 0.1 | 0.1# | 0.0 |
| | | | | | | K | | | | | | 0.6# | 0.0 | 0.1# | 0.0 |
| V | | | | | | | | | | W | | 0.6 | 0.2 | 0.4 | 0.1 |
| | | | | | | W | | | | | | 6.2 | 1.6 | 5.3 | 1.2 |
| | | | | | | L | | | | W | | 5.4 | 1.6 | 4.2 | 1.0 |
| | | | | | | L | | | | W | | 7.1 | 1.9 | 5.4 | 1.3 |
| V | | | | | | W | | | | | | 6.6 | 0.7 | 5.9 | 0.9 |
| V | | | | | | L | | | | W | | 10.4 | 1.3 | 8.0 | 1.6 |
| V | | | | | | W | | | | | | 6.7 | 0.9 | 5.6 | 1.0 |
| | | | | | | L | | | | W | | 9.2 | 1.0 | 7.0 | 1.9 |
| V | | | D | | | | | | | W | | 18.8 | 2.1 | 18.7 | 2.6 |
| V | | | | | | | | | | | | 16.3 | 1.8 | 15.7 | 2.6 |
| V | | | | | | L | | | | | | 12.2 | 1.1 | 11.7 | 2.2 |
| V | | | | | | L | | | | W | | 17.8 | 2.1 | 13.4 | 5.4 |
| V | | | | | | | | | | W | | 8.7 | 0.9 | 8.2 | 3.9 |
| V | | | | | | | | | | | | 7.5 | 0.9 | 7.2 | 1.9 |
| V | | | | | | L | | | | | | 8.4 | 0.9 | 6.5 | 1.4 |
| | | | | | | L | | | | W | | 14.9 | 1.6 | 12.1 | 4.8 |
| V | | | | | | K | | | | | | 8.6 | 1.0 | 8.2 | 1.4 |
| V | | | | | | K | | | | | | 4.9 | 0.6 | 3.9 | 0.7 |
| | | | | | | | | | | | | 3.9 | 0.7 | 4.5 | 0.7 |
| | | | | | | L | | | | W | | 18.8 | 1.7 | 18.2 | 3.4 |
| | | | | | | L | | | | W | | 16.4 | 1.5 | 11.9 | 4.0 |
| V | | | | | | W | | | | | | 19.7 | 2.2 | 17.4 | 3.8 |
| V | | | | | | W | | | | | | 21.9* | 5.3 | 22.0* | 8.9 |
| V | | | | | | W | | | | | | 18.7* | 4.2 | 19.0* | 6.8 |
| V | | | | | | W | | | | | | 20.1* | 6.2 | 19.9* | 7.4 |
| V | | | | | | W | | | | | | 19.5* | 4.5 | 18.8* | 6.6 |
| V | | | | | | W | | | | | | 4.1* | 1.1 | 4.1* | 1.5 |
| V | | | | | | W | | | | | | 22.0* | 5.7 | 23.2* | 9.1 |
| V | | | | | | W | | | | | | 20.0* | 5.8 | 18.9* | 7.1 |
| V | | | | | | W | | | | | | 14.0* | 3.4 | 11.2* | 4.4 |
| V | | | | | M | W | | | | | | 23.1* | 5.5 | 21.2* | 7.5 |
| V | | | | | | A | W | | | | | 18.6* | 5.0 | 18.2* | 6.8 |
| V | | | | | | W | S | | | | | 23.9* | 6.3 | 22.8* | 7.6 |
| V | | | | | | W | | S | | | | 17.0* | 4.0 | 16.5* | 5.9 |
| V | | | | | | W | | | T | | | 22.8* | 6.4 | 19.9* | 8.0 |
| V | | | | | | W | | | | V | | 15.7* | 3.9 | 13.7* | 5.1 |
| V | | | | | | A | W | S | S | T | A | 10.9* | 3.1 | 9.0* | 4.0 |
| V | | | | | | W | | | | | | 20.9* | 5.3 | 20.3* | 7.4 |
| V | | | | | | W | | | | | | 17.9* | 4.5 | 19.1* | 6.9 |
| V | | | | | | W | | | | | | 16.0* | 3.6 | 14.7* | 5.2 |
| V | | | | | | W | | | | | | 19.6* | 4.9 | 18.1* | 6.8 |
| V | | | | | | W | | | | | | 11.2* | 2.8 | 11.6* | 4.1 |
| V | | | | | | W | | | | | | 10.9* | 2.8 | 12.6* | 4.4 |
| V | | | | | | W | | | | | | 10.1* | 2.7 | 7.9* | 2.7 |
| V | | | | | | W | | | | | | 21.4* | 5.2 | 18.7* | 7.2 |
| V | | | | | M | A | W | S | S | T | | 18.3* | 4.6 | 13.3* | 4.3 |
| V | | | | | | W | | | | | | 11.9* | 2.1 | 9.3* | 2.9 |
| V | | | | | M | A | W | S | S | T | | 21.4* | 3.6 | 16.8* | 5.8 |
| V | | | | | M | A | W | S | S | T | | 18.8* | 4.4 | 12.3* | 3.5 |
| V | | | | | M | W | | | | | | 19.8* | 3.3 | 15.5* | 4.8 |
| V | | | | | M | W | | | | | | 18.7* | 3.4 | 15.1* | 4.6 |

TABLE 2-continued

| Example of multiple amino acid substitutions within 2A8. | | | | | | | | | | | | | |
|---|---|---|---|---|---|---|---|---|---|---|---|---|---|
| | S | | | L | | | | | W | 19.9* | 4.0 | 20.3* | 5.7 |
| | | | A | L | | | | | W | 4.4* | 1.3 | 6.1* | 1.7 |
| | | | | L | S | | | | W | 20.7* | 4.1 | 20.5* | 6.7 |
| | | | | L | | S | | | W | 14.2* | 2.7 | 15.6* | 4.2 |
| | | | | L | | | T | | W | 18.6* | 4.0 | 19.3* | 5.4 |
| | | | | L | | | | V | W | 10.2* | 2.1 | 13.6* | 4.6 |
| | | | | L | | | | | W | 4.0* | 0.9 | 4.6* | 1.3 |
| | | | | L | | | | | W | 3.9* | 1.2 | 3.0* | 1.0 |
| | | | | L | | | | | W | 18.1* | 4.3 | 18.2* | 5.8 |
| | | | | L | | | | | W | 17.8* | 4.2 | 16.9* | 5.0 |
| | | | | L | | | | | W | 13.6* | 2.8 | 10.6* | 3.6 |
| | | | | L | | | | | W | 13.5* | 2.8 | 6.5* | 3.3 |
| | | | | L | | | | | W | 9.0* | 2.0 | 4.7* | 2.3 |
| | | | | L | | | | | W | 16.6* | 3.8 | 9.3* | 4.3 |
| | | | | L | | | | | W | 11.7* | 2.9 | 7.9* | 4.6 |
| | | | | L | | | | | W | 16.2* | 3.9 | 12.1* | 6.0 |
| | | | | L | | | | | W | 12.1* | 2.8 | 7.7* | 3.8 |
| R | S | M | | L | S | | T | | W | 2.2* | 0.9 | 2.4* | 1.4 |
| | S | M | | L | S | | T | | W | 11.4* | 2.7 | 7.1* | 3.6 |
| | | M | | L | S | | T | | W | 9.8* | 2.5 | 5.9* | 2.0 |
| | S | M | | L | S | | T | | W | 19.6* | 3.5 | 21.4* | 9.6 |
| | | M | | L | S | | T | | W | 18.0* | 4.9 | 15.4* | 7.6 |

Provided in Table 3 are several examples of single and/or double amino acid substitutions introduced into the heavy and/or light chain of 4B7. The expression level of the variants was analyzed in quadruples in the quantification ELISA. After normalization to the respective expression level, performance was analyzed in quadruples in the competitive ELISA on human TFPI and in the equilibrium ELISA on murine TFPI followed by determination of variant to wild-type ratios. Errors were calculated by error propagation from the standard deviations.

TABLE 3

Analysis of single and double amino acid substitutions within 4B7.

| 4B7 variants | hTFPI variant/wild-type | error | mTFPI variant/wild-type | error |
|---|---|---|---|---|
| HC_N32D | 3.8 | 0.7 | 6.0 | 2.9 |
| HC_N32E | 3.2 | 1.0 | 2.1 | 0.3 |
| HC_S33G | 1.5 | 0.3 | 6.5 | 1.2 |
| HC_S57K | 1.7 | 0.4 | 6.5 | 1.1 |
| HC_S57R | 2.0 | 0.4 | 6.6 | 1.4 |
| HC_D62I | 9.8 | 1.6 | 44.4 | 11.6 |
| HC_D62R | 32.3 | 4.5 | 230.2 | 34.1 |
| HC_D62L | 6.8 | 1.2 | 22.9 | 6.1 |
| HC_D62Q | 20.6 | 2.8 | 142.5 | 28.0 |
| HC_D62S | 29.3 | 4.3 | 146.5 | 40.4 |
| HC_H103D | 2.4 | 0.4 | 12.9 | 2.0 |
| HC_H103G | 1.4 | 0.3 | 10.7 | 2.0 |
| HC_Y112D | 2.9 | 0.6 | 5.7 | 1.3 |
| LC_S32R | 4.2 | 0.7 | 7.8 | 1.5 |
| LC_S32Y | 2.0 | 0.4 | 6.7 | 1.2 |
| LC_D33F | 5.3 | 1.3 | 7.0 | 2.6 |
| LC_D33R | 3.6 | 0.7 | 7.2 | 1.9 |
| LC_N35I | 3.6 | 0.7 | 7.1 | 1.5 |
| LC_N35L | 2.1 | 1.0 | 6.0 | 1.3 |
| LC_N35T | 5.4 | 1.0 | 3.4 | 1.1 |
| LC_Y37F | 3.6 | 0.7 | 1.9 | 0.6 |
| LC_S57Y | 1.6 | 0.4 | 2.2 | 0.4 |
| LC_S61C | 3.1 | 0.5 | 15.3 | 4.2 |
| LC_D97M | 2.4 | 0.5 | 1.3 | 0.4 |
| LC_D97T | 1.8 | 0.3 | 5.5 | 1.6 |
| HC_N61G | 2.2 | 0.5 | 1.4 | 0.3 |
| HC_D62V | 31.9 | 5.6 | 95.0 | 20.4 |
| HC_D62N | 52.3 | 9.5 | 146.4 | 28.9 |
| HC_H107M | 8.1 | 1.6 | 5.6 | 1.7 |

TABLE 3-continued

Analysis of single and double amino acid substitutions within 4B7.

| 4B7 variants | hTFPI variant/wild-type | error | mTFPI variant/wild-type | error |
|---|---|---|---|---|
| LC_F31I | 9.1 | 2.1 | 23.6 | 4.3 |
| LC_F31M | 1.7 | 0.4 | 1.3 | 0.4 |
| LC_N35V LC_G56D | 1.9 | 0.4 | 8.2 | 1.7 |
| LC_N35L LC_G56A | 3.1 | 0.7 | 6.9 | 1.6 |
| LC_D33F LC_Y54F | 4.3 | 0.9 | 7.9 | 1.9 |
| HC_S30R HC_S57K | 1.6 | 0.3 | 6.6 | 1.1 |
| HC_N61G HC_D62V | 8.0 | 1.1 | 31.1 | 9.1 |
| HC_H107M LC_F31I | 3.7 | 0.7 | 9.2 | 2.7 |
| HC_G109A LC_D33R | 3.8 | 0.6 | 8.0 | 1.3 |
| HC_N61T LC_G167C | 2.8 | 0.4 | 6.4 | 1.6 |
| HC_K58M HC_D62N | 6.6 | 1.2 | 15.2 | 4.5 |

Provided in Table 4 are some examples of combinations of amino acid substitutions within 4B7 TFPI antibodies. While not every combination is provided in Table 4, it is contemplated that the TFPI antibody may comprise any combination of modifications provided. The expression level of variants was analyzed in quadruples in the quantification ELISA. If not otherwise indicated, variants were normalized to the respective expression level and performance was analyzed in quadruples in the competitive ELISA on human and murine TFPI followed by calculation of variant to reference (HC_D62R) ratios. In cases were a different reference was used and variants were analyzed without prior normalization, values are marked with "*". For these variants, the value listed in the table was calculated by multiplying the ratios variant/alternative reference with alternative reference/HC_D62R. Errors were calculated by error propagation from the standard deviations. nb: no binding detected under assay conditions used.

TABLE 4

Example of multiple amino acid substitutions within 4B7.

| HC_4B7 | | | | | | | | | | LC_4B7 | | | | | | | | | | | |
|---|---|---|---|---|---|---|---|---|---|---|---|---|---|---|---|---|---|---|---|---|---|
| Q1 | N32 | S37 | G44 | I53 | K55 | D62 | H103 | H107 | Y112 | M4 | V30 | F31 | S32 | D33 | N35 | T36 | Y37 | N39 | L42 | K44 | Q50 |
| | D | | | | | R | | | D | | | | R | | I | | | | | | |
| | D | | | | | R | | M | D | | | I | R | | I | | | | | | |
| | D | | | | | R | | | D | | | | | R | I | | | | | | |
| | D | | | | | S | | M | D | | | | R | R | T | | | | | | |
| | D | | | | | R | D | | | | | I | | R | | | | | | | |
| | | | | | | R | | M | D | | | | | F | I | | | | | | |
| | D | | | | | R | | | D | | | | | F | I | | | | | | |
| | D | | | | | R | | | D | | | I | | F | I | | | | | | |
| | | | | | | R | | M | D | | | M | | F | | | | | | | |
| | | | | | | R | | M | D | | | I | | R | I | | | | | | |
| | D | | | | | R | D | M | D | | | | R | | T | | | | | | |
| | D | | | | | Q | | | D | | | M | R | F | I | | | | | | |
| | D | | | | | R | | | D | | | | R | F | I | | | | | | |
| | D | | | | | R | | M | D | | | | R | F | T | | | | | | |
| | D | | | | | Q | | M | D | | | | | R | T | | | | | | |
| | D | | | | | Q | | M | D | | | | R | | T | | | | | | |
| | D | | | | | R | | M | | | | | R | R | I | | | | | | |
| | D | | | | | R | | M | D | | | I | | R | I | | | | | | |
| | D | | | | | R | | | D | | | M | R | R | I | | | | | | |
| | | | | | | R | | | D | | | | | F | I | | | | | | |
| | D | | | | | R | | M | D | | | I | | R | | | | | | | |
| | D | | | | | R | | M | D | | | M | L | R | I | | | | | | |
| | D | | | | | R | | M | D | | | M | | F | I | | | | | | |
| | D | | | | | Q | | M | D | | | M | R | F | I | | | | | | |
| | D | | | | | R | | | D | | | | | | T | | | | | | |
| | D | | | | | R | | M | D | | | M | | R | | | | | | | |
| | D | | | | | R | | M | D | | | M | | R | I | | | | | | |
| | D | | | | | R | | M | D | | | M | | F | T | | | | | | |
| | | | | | | Q | | | D | | | | R | F | I | | | | | | |
| | D | | | | | Q | | | D | | | | R | R | I | | | | | | |
| | D | | | | | R | | M | D | | | I | | | I | | | | | | |
| | D | | | | | Q | | M | D | | | | R | F | I | | | | | | |
| | D | | | | | Q | | | D | | | I | | F | I | | | | | | |
| | | | | | | R | | M | D | | | M | | F | I | | | | | | |
| | D | | | | | Q | | M | D | | | I | R | R | I | | | | | | |
| | | | | | | R | | M | D | | | | | | T | | | | | | |
| | D | | | | | R | | M | D | | | M | R | R | | | | | | | |
| | D | | | | | R | | M | D | | | I | R | F | I | | | | | | |
| | D | | | | | R | D | M | D | | | | R | | | | | | | | |
| | D | | | | | Q | | | D | | | | R | R | I | | | | | | |
| | | | | | | R | | M | D | | | | R | F | I | | | | | | |
| | D | | | | | R | | M | D | | | I | R | F | T | | | | | | |
| | D | | | | | Q | | M | D | | | | R | R | | | | | | | |
| | D | | | | | R | | M | D | | | M | R | R | I | | | | | | |
| | D | | | | | R | | M | D | | | | R | | T | | | | | | |
| | D | | | | | R | | M | D | | | M | R | F | | | | | | | |
| | D | | | | | R | | M | D | | | M | R | R | T | | | | | | |
| | | | | | | S | | M | D | | | | R | F | I | | | | | | |
| | | | | | | R | | M | D | | | I | R | F | I | | | | | | |
| | D | | | | | Q | | M | D | | | M | | F | T | | F | | | | |
| | D | | | | | R | | | D | | | | R | R | | | | | | | |
| | D | | | | | R | | M | D | | | | | F | T | | F | | | | |
| | D | | | | | Q | | M | D | | | | | | I | | | | | | |
| | D | | | | | Q | | M | D | | | | R | F | | | | | | | |
| | D | | | | | R | | M | D | | | | | R | | | | | | | |
| | | | | | | Q | | M | D | | | | | F | I | | | | | | |
| | D | | | | | R | | M | D | | | | | R | I | | | | | | |
| | D | | | | | R | | M | D | | | | R | | T | | | | | | |
| | D | | | | | R | | M | D | | | | | R | T | | | | | | |
| | D | | | | | R | | | D | | | | R | F | I | | | | | | |
| | D | | | | | R | | M | D | | | M | R | F | I | | | | | | |
| | | | | | | R | | | D | | | | R | F | I | | | | | | |
| | D | | | | | R | | | D | L | | | R | F | I | | | | | | |
| | D | | | | | R | | | D | I | | | R | F | I | | | | | | |
| | D | | | | | R | | | D | | L | | R | F | I | | | | | | |
| | D | | | | | R | | | D | | | H | R | F | I | | | | | | |
| | D | | | | | R | | | D | | | Y | R | F | I | | | | | | |
| | D | | | | | R | | | D | | | | R | F | I | N | | | | | |
| | D | | | | | R | | | D | | | | R | F | I | | | D | | | |
| | D | | | | | R | | | D | | | | R | F | I | | | | Q | | |
| | D | | | | | R | | | D | | | | R | F | I | | | | | R | |
| | D | | | | | R | | | D | | | | R | F | I | | | | | | R |
| | D | | | | | R | | | D | | | | R | F | I | | | | | | |
| | D | | | | | R | | | D | | | | R | F | I | | | | | | |

TABLE 4-continued

Example of multiple amino acid substitutions within 4B7.

| | | | | | | | | | | | | | | LC_4B7 | | | | | | hTFPI | | mTFPI | |
|---|---|---|---|---|---|---|---|---|---|---|---|---|---|---|---|---|---|---|---|---|---|---|---|
| | | | | | | | | | | | | | | L51 | K55 | G56 | A60 | D97 | S98 | variant/HC_D62R | error | variant/HC_D62R | error |
| | D | | | | R | | D | | | R | F | I | | | | | | | | 26.1 | 2.2 | 30.1 | 4.3 |
| | D | | | | R | | D | | | R | F | I | | | | | | | T | 18.2 | 3.6 | 8.7 | 1.4 |
| | D | | | | R | | D | | | R | F | I | | | | | | | | 22.9 | 2.5 | 19.5 | 3.2 |
| E | D | | | | R | | D | | | R | F | I | | | | | | | | 19.6 | 1.9 | 20.3 | 3.2 |
| | D | N | | | R | | D | | | R | F | I | | | | | | | | 13.6 | 1.4 | 14.6 | 2.4 |
| | D | | S | | R | | D | | | R | F | I | | | | | | | | 20.0 | 3.4 | 36.6 | 9.8 |
| | D | | | T | R | | D | | | R | F | I | | | | | | | T | 25.5 | 1.7 | 15.9 | 2.6 |
| | D | | | | R | Y | D | | | R | F | I | | | | | | | T | 23.3 | 3.1 | 11.9 | 2.2 |
| | D | | | | K | | D | | | R | F | I | | | | | | | | 24.2 | 1.8 | 31.3 | 5.0 |
| | D | | | | Q | | D | | | R | F | I | | | | | | | | 22.0 | 2.2 | 35.4 | 5.0 |
| E | D | | S | | Y | R | D | | L | R | F | I | N | | | | | | | 14.0 | 1.7 | 18.4 | 2.7 |
| | D | | | | R | | D | | L | R | F | I | N | | | | | | | 20.8 | 1.6 | 15.8 | 2.1 |
| E | D | | S | | Y | R | D | | | R | | F | I | | | | | | | 29.7 | 2.2 | 42.0 | 5.9 |
| | D | | | | Q | | D | L | I | | F | I | | | | | | | | 29.2 | 1.9 | 44.1 | 7.2 |
| | D | | | | Q | | D | | I | | F | I | N | | | | | | | 23.7 | 1.4 | 18.8 | 3.2 |
| | D | | | | Q | | D | | I | | F | I | | | | | Q | R | | 25.0 | 2.0 | 27.1 | 5.0 |
| | D | | | | Q | | D | | I | | F | I | | | | | | | | 12.9 | 1.4 | 16.1 | 2.4 |
| | D | | | | Q | | D | | I | | F | I | | | | | | | | 29.8 | 2.9 | 43.0 | 7.0 |
| | D | | | | Q | | D | | I | | F | I | | | | | | | | 15.8 | 1.0 | 11.2 | 2.0 |
| | D | | | T | Q | | D | | I | | F | I | | | | | | | | 20.3 | 1.5 | 20.8 | 3.6 |
| | D | | | | Y | Q | D | | I | | F | I | | | | | | | | 30.1 | 1.6 | 27.9 | 6.9 |
| E | D | | S | | Y | R | D | | L | R | | I | N | | | | | | T | 32.2 | 3.1 | 26.7 | 4.5 |
| | D | | | | R | | D | | L | R | | I | N | | | | | | | 28.4 | 2.2 | 46.8 | 7.6 |
| E | D | | S | | Y | R | D | | | R | | I | | | | | | | T | 19.0 | 1.8 | 12.0 | 2.9 |
| | | | | | | | | | | | | | | | | | | | T | 26.0 | 3.2 | 9.5 | 2.9 |
| | | | | | | | | | | | | | | | | | | | | 26.9 | 2.9 | 24.6 | 4.7 |
| | | | | | | | | | | | | | | | | | | | | 21.3 | 1.8 | 23.0 | 8.6 |
| | | | | | | | | | | | | | | | | | | | | 29.9 | 2.2 | 34.3 | 5.6 |
| | | | | | | | | | | | | | | | | | | | | 23.6 | 1.9 | 38.1 | 5.7 |
| | | | | | | | | | | | | | | | | | | | | 21.4 | 1.5 | 23.5 | 4.4 |
| | | | | | | | | | | | | | | | | | | | | 28.8 | 2.6 | 30.0 | 5.2 |
| | | | | | | | | | | | | | | | | | | | | 24.7 | 4.2 | 46.6 | 6.2 |
| | | | | | | | | | | | | | | | | | | | | 22.4 | 3.0 | 14.0 | 5.6 |
| | | | | | | | | | | | | | | | | | | | | 30.9 | 3.0 | 47.0 | 7.9 |
| | | | | | | | | | | | | | | | | | | | T | 20.2 | 1.7 | 11.5 | 1.9 |
| | | | | | | | | | | | | | | | | | | | T | 20.1 | 2.1 | 19.4 | 3.4 |
| | | | | | | | | | | | | | | | | | | | | 18.6 | 1.4 | 13.9 | 2.1 |
| | | | | | | | | | | | | | | | | | | | T | 28.7 | 3.2 | 20.6 | 5.0 |
| | | | | | | | | | | | | | | | | | | | | 17.7 | 1.4 | 16.0 | 2.9 |
| | | | | | | | | | | | | | | | | | | | T | 17.2 | 1.0 | 13.4 | 1.9 |
| | | | | | | | | | | | | | | | | | | | | 24.1 | 2.5 | 50.3 | 6.6 |
| | | | | | | | | | | | | | | | | | | | | 29.5 | 2.9 | 19.7 | 3.5 |
| | | | | | | | | | | | | | | | | | | | | 24.9 | 2.3 | 24.7 | 3.2 |
| | | | | | | | | | | | | | | | | | | | T | 16.9 | 1.5 | 9.6 | 1.7 |
| | | | | | | | | | | | | | | | | | | | T | 27.7 | 2.5 | 15.8 | 2.5 |
| | | | | | | | | | | | | | | | | | | | T | 21.9 | 1.7 | 16.5 | 3.7 |
| | | | | | | | | | | | | | | | | | | | | 17.0 | 2.1 | 18.7 | 2.5 |
| | | | | | | | | | | | | | | | | | | | | 18.2 | 3.5 | 31.7 | 5.7 |
| | | | | | | | | | | | | | | | | | | | T | 20.4 | 2.5 | 18.2 | 2.6 |

TABLE 4-continued

Example of multiple amino acid substitutions within 4B7.

| | | | | | | | | | |
|---|---|---|---|---|---|---|---|---|---|
| | | | | | | | 19.4 | 3.2 | 35.3 | 5.6 |
| | | | | | | | 14.8 | 2.7 | 7.2 | 1.3 |
| | | | | | | | 35.7 | 4.3 | 57.5 | 9.1 |
| | | | | | | | 22.2 | 1.6 | 16.4 | 2.5 |
| | | | | | | | 23.2 | 1.7 | 16.9 | 3.8 |
| | | | | | | | 25.3 | 2.6 | 20.3 | 2.6 |
| | | | | | | | 22.7 | 1.4 | 31.7 | 5.1 |
| | | | | | T | | 29.1 | 1.8 | 28.1 | 4.9 |
| | | | | | | | 25.3 | 2.8 | 29.3 | 4.8 |
| | | | | | | | 28.2 | 2.7 | 29.3 | 4.5 |
| | | | | | T | | 26.2 | 2.9 | 40.0 | 6.1 |
| | | | | | | | 27.0 | 1.5 | 32.3 | 4.9 |
| | | | | | | | 21.9 | 2.0 | 39.9 | 5.9 |
| | | | | | T | | 21.3* | 6.7 | 23.9* | 4.7 |
| | | | | | T | | 19.3* | 5.3 | 12* | 2.8 |
| | | | | | T | | 26.1* | 7.6 | 42.2* | 10.1 |
| | | | | | T | | 22.1* | 6.8 | 15.2* | 3.2 |
| | | | | | T | | 27.9* | 9.8 | 39.7* | 10.4 |
| | | | | | T | | 25.2* | 7.6 | 35.4* | 8.8 |
| | | | | | T | | 1.3* | 0.5 | nb | 0.0 |
| | | | | | T | | 26.9* | 7.6 | 43* | 10.5 |
| | | | | | T | | 26* | 8.1 | 40.1* | 9.1 |
| | | | | | T | | 25.9* | 7.4 | 39.4* | 10.4 |
| R | | | | | T | | 11.2* | 3.6 | 5.2* | 1.5 |
| | L | | | | T | | 7.8* | 2.0 | nb | 0.0 |
| | | V | | | T | | 12.1* | 3.4 | nb | 0.0 |
| | | | D | | T | | 19.1* | 6.2 | 14.3* | 3.6 |
| | | | | | T | H | 17.9* | 5.3 | 7.1* | 1.7 |
| | | | | | T | | 26.7* | 9.0 | 39.8* | 8.9 |
| | | | | | T | | 1.9* | 0.7 | nb | 0.0 |
| | | | | | T | | 26.5* | 8.1 | 41.5* | 10.2 |
| | | | | | T | | 19.6* | 6.0 | 8.3* | 2.3 |
| | | | | | T | | 25.6* | 8.5 | 42.8* | 10.4 |
| | | | | | T | | 22.7* | 7.1 | 38.8* | 8.8 |
| | | | | | T | | 23.2* | 7.0 | 40* | 8.8 |
| | | | | | T | | 20.4* | 5.3 | 29.4* | 6.3 |
| | | | | | T | | 23.9* | 4.9 | 28.4* | 8.2 |
| | | | | | T | | 26.3* | 4.8 | 45.1* | 9.6 |
| | | | | | | | 22.9* | 8.0 | 24.6* | 12.8 |
| | | | | | | | 27.3* | 8.9 | 46.3* | 23.5 |
| | | | | | | | 21.4* | 6.9 | 16.7* | 8.9 |
| | | | | | | | 22.8* | 7.9 | 18.5* | 9.6 |
| | | | | | T | | 14.4* | 4.2 | 4.6* | 2.5 |
| | | | | | | H | 13.5* | 4.8 | nb | 0.0 |
| | | | | | | | 5.7* | 1.5 | nb | 0.0 |
| | | | | | | | 25.6* | 9.0 | 26.2* | 13.3 |
| | | | | | | | 23* | 5.0 | 9.9* | 3.3 |
| | | | | | | | 25* | 4.3 | 7* | 4.2 |
| | | | | | | | 22.6* | 3.9 | 25.5* | 5.8 |

Example 4

Purification of Antibodies

Cells were harvested by centrifugation at 9000 rpm for 30 min at 4° C. and stored at −20° C. Supernatant was buffered-exchanged with buffer A (50 mM $NaH_2PO_4$, 300 mM NaCl, 10 mM imidazole pH8.0), concentrated and purified using a two-step purification procedure. Briefly, 100 ml concentrated supernatant was loaded on a 5 ml Ni-NTA superflow column (Qiagen, 1018142) washed first with 5× column volumes of buffer A followed by 5× column volumes of 4.3% buffer B (50 mM $NaH_2PO_4$, 300 mM NaCl, 250 mM imidazole pH8.0) and eluted with 7 volumes of buffer B. Fractions are combined and dialyzed in PBS. In a second purification step the Ni-NTA purified antibodies were incubated with a light chain-specific affinity matrix, i.e. capture select lambda or kappa (BAC 0849.010 and BAC 0833.10, respectively) for 2A8 and 4B7, respectively. After incubation at 4° C. over night the matrix was loaded into a column, washed with 5 volumes of PBS, 5 volumes of 500 mM arginine 100 mM $NaH_2PO_4$, 100 mM NaCl pH6.0 and again 5 volumes of PBS. Antibodies were eluted with 6 volumes of 100 mM glycine pH3.0 followed by 3 volumes of 100 mM glycine pH2.0 into 1/10 of total volume of 1M HEPES pH 7.5 to neutralize the elutes. Finally, eluates were dialyzed in PBS over night at 4° C. Purified antibodies were analyzed by SDS-PAGE and mass spectrometry.

Example 5

Measure Affinity of Antibody Binding to TFPI Using Surface Plasmon Resonance (Biacore)

Either human or mouse TFPI, was immobilized on the surface for analysis. The CM5-chips and the amine coupling kit (GE HealthCare) were used for the immobilization of the ligand according to the instructions from the manufacturer. The amount of immobilized TFPI was approximately 70 RU to adapt to the mass of antibody that could generate RMax of 100 RU. Parental and affinity matured anti-TFPI antibodies were in the mobile phase. The affinity determination was performed with at least five different concentrations (0.1, 0.4, 1.6, 6.4 and 25 nM) of the purified antibodies.

By analyzing antibody variants that contain single mutations in CDR regions, we identified many clones that had a higher signal in the Elisa binding assay. Selected clones were purified and their affinity to human or mouse TFPI was analyzed using Biacore. As shown in Table 5 and Table 6, these clones have higher affinity to TFPI than do the parental antibodies 2A8 or 4B7. Although some of the 2A8 mutants have slower associate rate (ka) than the parental antibody 2A8, all of these mutants have much slower dissociate rate (kd) than 2A8. Overall, these single mutations increase affinity of 2A8 in the range from 1.47 fold to 7.22 fold on human TFPI, and 1.71 fold to 7.20 fold on mouse TFPI. When we analyzed 4B7 variants, the D62R mutation in heavy chain CDR2 domain significantly increased the signal. This clone was chosen for affinity measurement. As shown in Table 5 and Table 6, this single mutation increases 4B7's affinity to human TFPI from 11.1 nM to 58.2 pM, a 191 fold improvement. The slow dissociate rate (kd) of 4B7HcD62R mainly contributes to its affinity improvement, from $8.40 \times 10^{-3}$/s of 4B7 to $1.65 \times 10^{-4}$ of 4B7HcD62R, approximately 50 fold improvement. Similarly, this mutation increases the 4B7's affinity to mouse TFPI from 58.6 nM to 427 pM, a 137-fold improvement.

TABLE 5

Affinity of selected 2A8 or 4B7 variants (single mutation) on human TFPI

| Sample | Clone | ka (1/Ms) | kd (1/s) | KD (M) | Improvement |
|---|---|---|---|---|---|
| 2A8-1 | HC_G33P | 2.71E+06 | 2.24E-03 | 8.27E-10 | 2.70 |
| 2A8-2 | HC_S31P | 2.91E+06 | 3.33E-03 | 1.15E-09 | 1.95 |
| 2A8-3 | HC_S31V | 3.84E+06 | 1.43E-03 | 3.73E-10 | 6.00 |
| 2A8-4 | HC_S35D | 4.01E+06 | 3.80E-03 | 9.50E-10 | 2.35 |
| 2A8-6 | HC_I51E | 1.29E+06 | 1.62E-03 | 1.26E-09 | 1.78 |
| 2A8-7 | HC_S54F | 2.81E+06 | 2.04E-03 | 7.27E-10 | 3.08 |
| 2A8-8 | HC_S55R | 4.30E+06 | 3.94E-03 | 9.17E-10 | 2.44 |
| 2A8-9 | HC_K99L | 2.60E+06 | 8.03E-04 | 3.09E-10 | 7.22 |
| 2A8-10 | HC_K99V | 2.55E+06 | 2.54E-03 | 9.95E-10 | 2.25 |
| 2A8-11 | LC_A32N | 2.70E+06 | 4.10E-03 | 1.52E-09 | 1.47 |
| 2A8-12 | HC_I51D | 3.61E+06 | 4.95E-03 | 1.37E-09 | 1.63 |
| 2A8-13 | LC_N51V | 4.26E+06 | 2.20E-03 | 5.18E-10 | 4.32 |
| 2A8-14 | LC_Y48F | 2.64E+06 | 3.00E-03 | 1.14E-09 | 1.97 |
| 2A8-15 | LC_D91K | 4.33E+06 | 2.09E-03 | 4.82E-10 | 4.64 |
| 2A8-16 | LC_D91L | 4.41E+06 | 4.40E-03 | 9.99E-10 | 2.24 |
| 2A8-17 | LC_D91W | 3.86E+06 | 4.32E-03 | 1.12E-09 | 2.00 |
| 2A8-20 | 2A8wt | 3.13E+06 | 7.00E-03 | 2.24E-09 | 1.00 |
| 4B7HcD62R | HC_D62R | 2.83E+06 | 1.65E-04 | 5.82E-11 | 190.83 |
| 4B7 | 4B7wt | 7.56E+05 | 8.40E-03 | 1.11E-08 | 1.00 |

TABLE 6

Affinity of selected 2A8 and 4B7 variants (single mutation) on mouse TFPI

| Sample | Clone | ka (1/Ms) | kd (1/s) | KD (M) | Improvement |
|---|---|---|---|---|---|
| 2A8-1 | HC_G33P | 9.12E+05 | 1.45E-03 | 1.59E-09 | 2.21 |
| 2A8-2 | HC_S31P | 1.53E+06 | 3.16E-03 | 2.06E-09 | 1.71 |
| 2A8-3 | HC_S31V | 3.39E+06 | 2.02E-03 | 5.95E-10 | 5.91 |
| 2A8-4 | HC_S35D | 1.25E+06 | 2.46E-03 | 1.98E-09 | 1.78 |
| 2A8-7 | HC_S54F | 8.84E+05 | 1.83E-03 | 2.07E-09 | 1.69 |
| 2A8-9 | HC_K99L | 1.56E+06 | 7.59E-04 | 4.88E-10 | 7.20 |
| 2A8-17 | LC_D91W | 2.86E+06 | 2.32E-03 | 8.14E-10 | 4.32 |
| 2A8wt | 2A8wt | 1.47E+06 | 5.17E-03 | 3.51E-09 | 1.00 |
| 4B7HcD62R | HC_D62R | 8.58E+06 | 3.67E-03 | 4.27E-10 | 137.00 |
| 4B7wt | 4B7wt | 2.18E+06 | 1.28E-01 | 5.86E-08 | 1.00 |

Next, binding affinity of multiple mutations within 2A8 and 4B7 was investigated. As shown in Table 7(a) and Table 8(a), the mutants of 2A8 that contain multiple mutations in CDR domains have higher affinity than single mutated 2A8 on both human TFPI and mouse TFPI binding. For example, 2A8-200 has 53.7 fold higher affinity than 2A8 on human TFPI binding, and 55.4 fold higher affinity on mouse TFPI binding. As shown in Table 7(b) and Table 8(b), the mutants of 4B7 that contain multiple mutations in CDR domains have higher affinity than single mutated 4B7 on both human TFPI and mouse TFPI binding. Those variants from the parental 2A8 and 4B7 sequences provided in Tables 7 and 8 have also been provided in the sequence listing. SEQ ID NOs: 5-11 correspond to the heavy chain variants of 2A8 listed in Table 7 and 8. SEQ ID NOs: 12-18 correspond to the light chain variants of 2A8. SEQ ID NOs: 19-26 correspond to the heavy chain variants of 4B7 listed in Table 7 and 8. SEQ ID NOs: 27-34 correspond to the light chain variants of 4B7.

TABLE 7(a)

Affinity of selected 2A8 variants (multiple mutations) on human TFPI

| | 2A8 HC | | | | | | | | 2A8 LC | | | | | | | | | | |
|---|---|---|---|---|---|---|---|---|---|---|---|---|---|---|---|---|---|---|---|
| Samples | Q1 | R30 | S31 | S35 | I51 | S55 | S56 | K99 | D1 | I2 | A13 | S21 | R28 | N29 | Y48 | N51 | G56 | E80 | S89 |
| 2A8-127 | | | | D | | | | L | | | | | | | F | V | D | | |
| 2A8-143 | | | | D | | R | | L | | | | | | | F | V | | | |
| 2A8-200 | | | | D | | R | | L | | | | | | | F | V | | | |
| 2A8-216 | | | V | | D | R | | V | | | | | | | F | | | | |
| 2A8-227 | | | | D | | | | L | | | | | | | F | | | | |
| 2A8-g200 | E | S | | D | | R | G | L | S | Y | S | T | P | K | F | V | | M | A |
| 2A8-g216 | | | V | | D | R | | V | S | Y | S | T | P | K | F | S | | M | |
| 2A8 wt | | | | | | | | | | | | | | | | | | | |

| | 2A8 LC | | | | | | | | KD fold |
|---|---|---|---|---|---|---|---|---|---|
| Samples | D91 | D92 | G93 | V94 | V96 | ka (1/Ms) | kd (1/s) | KD (M) | improvement |
| 2A8-127 | | | | | W | 1.68E+06 | 1.41E−04 | 8.41E−11 | 22 |
| 2A8-143 | L | | | | W | 2.88E+06 | 1.05E−04 | 3.64E−11 | 50.9 |
| 2A8-200 | W | | | | | 2.87E+06 | 9.88E−05 | 3.44E−11 | 53.7 |
| 2A8-216 | L | | | | W | 3.29E+06 | 1.54E−04 | 4.67E−11 | 39.6 |

TABLE 7(a)-continued Affinity of selected 2A8 variants (multiple mutations) on human TFPI

| | | | | | | | | | |
|---|---|---|---|---|---|---|---|---|---|
| 2A8-227 | L | | | | W | 3.28E+06 | 1.23E−04 | 3.75E−11 | 49.4 |
| 2A8-g200 | W | S | S | T | | 6.17E+05 | 3.61E−05 | 5.84E−11 | 31.7 |
| 2A8-g216 | L | S | | T | W | 1.45E+06 | 5.29E−05 | 3.65E−11 | 50.7 |
| 2A8 wt | | | | | | 2.05E+06 | 3.80E−03 | 1.85E−09 | 1 |

TABLE 7(B)

Affinity of selected 4B7 variants (multiple mutations) on human TFPI

| | 4B7 HC | | | | | | 4B7 LC | | | | | | | | KD fold |
|---|---|---|---|---|---|---|---|---|---|---|---|---|---|---|---|
| Samples | Q1 | N32 | G44 | K55 | D62 | Y112 | F31 | S32 | D33 | N35 | D97 | ka (1/Ms) | kd (1/s) | KD (M) | improvement |
| B18.5 | | D | | | Q | D | I | | F | I | | 1.23E+06 | 3.18E−05 | 2.60E−11 | 428.2 |
| B2.0 | | D | | | R | D | | R | F | I | T | 7.46E+06 | 3.81E−05 | 5.10E−12 | 2177.8 |
| B27.1 | | D | | | R | D | | | | T | T | 2.78E+06 | 3.53E−05 | 1.27E−11 | 874.9 |
| B32.5 | | | | | R | D | | | F | I | | 2.15E+06 | 3.19E−05 | 1.48E−11 | 748.7 |
| B41.2 | | D | | | R | D | | R | F | I | | 3.46E+06 | 2.47E−05 | 7.16E−12 | 1552.7 |
| B9.7 | | D | | | R | D | | R | | I | | 2.97E+06 | 2.61E−05 | 8.78E−12 | 1266.2 |
| gB9.7 | E | D | S | Y | R | D | | R | | I | | 9.38E+05 | 9.55E−06 | 1.02E−11 | 1091.5 |
| gB9.7-IgG | | D | S | Y | R | D | | R | | I | | 2.03E+06 | 1.56E−05 | 7.65E−12 | 1450.9 |
| 4B7 | | | | | | | | | | | | 7.56E+05 | 8.40E−03 | 1.11E−08 | 1 |

TABLE 8(a)

Affinity of selected 2A8 variants (multiple mutations) on mouse TFPI

| | 2A8 HC | | | | | | | |
|---|---|---|---|---|---|---|---|---|
| Sample | Q1 | R30 | S31 | S35 | I51 | S55 | S56 | K99 |
| 2A8-127 | | | | D | | | | L |
| 2A8-143 | | | | D | | R | | L |
| 2A8-200 | | | | D | | R | | L |
| 2A8-216 | | | V | | D | R | | V |
| 2A8-227 | | | | D | | | | L |
| 2A8-g200 | E | S | | D | | R | G | L |
| 2A8-g216 | | | V | | D | R | | V |
| 2A8 wt | | | | | | | | |

| | 2A8 LC | | | | | | | |
|---|---|---|---|---|---|---|---|---|
| Sample | D1 | I2 | A13 | S21 | R28 | N29 | Y48 | N51 |
| 2A8-127 | | | | | | | F | V |
| 2A8-143 | | | | | | | F | V |
| 2A8-200 | | | | | | | F | V |
| 2A8-216 | | | | | | | F | |
| 2A8-227 | | | | | | | F | |
| 2A8-g200 | S | Y | S | T | P | K | F | V |
| 2A8-g216 | S | Y | S | T | P | K | F | S |
| 2A8 wt | | | | | | | | |

| | 2A8 LC | | | | | | | |
|---|---|---|---|---|---|---|---|---|
| Sample | G56 | E80 | S89 | D91 | D92 | G93 | V94 | V96 |
| 2A8-127 | D | | | | | | | W |
| 2A8-143 | | | | L | | | | W |
| 2A8-200 | | | | W | | | | |
| 2A8-216 | | | | L | | | | W |
| 2A8-227 | | | | L | | | | W |
| 2A8-g200 | | M | A | W | S | S | T | |
| 2A8-g216 | | M | | L | S | | T | W |
| 2A8 wt | | | | | | | | |

TABLE 8(a)-continued

| Affinity of selected 2A8 variants (multiple mutations) on mouse TFPI | | | | |
|---|---|---|---|---|
| Sample | Ka (1/Ms) | Kd (1/s) | KD (M) | KD feld improvement |
| 2A8-127 | 8.24E+05 | 1.47E−03 | 1.78E−10 | 18.5 |
| 2A8-143 | 1.40E+06 | 1.25E−03 | 6.78E−11 | 48.5 |
| 2A8-200 | 1.04E+06 | 6.19E−04 | 5.94E−11 | 55.4 |
| 2A8-216 | 4.19E+06 | 2.16E−04 | 5.15E−11 | 63.9 |
| 2A8-227 | 6.91E+06 | 1.06E−03 | 1.53E−10 | 21.4 |
| 2A8-g200 | 1.15E+06 | 1.39E−04 | 1.21E−10 | 27.3 |
| 2A8-g216 | 9.84E+05 | 7.78E−05 | 7.91E−11 | 41.6 |
| 2A8 wt | 9.40E+05 | 3.10E−03 | 3.29E−09 | 1 |

TABLE 8(B)

Affinity of selected 4B7 variants (multiple mutations) on mouse TFPI

| | 4B7 HC | | | | | | 4B7 LC | | | | | | | | KD fold |
|---|---|---|---|---|---|---|---|---|---|---|---|---|---|---|---|
| Samples | Q1 | N32 | G44 | K55 | D62 | Y112 | F31 | S32 | D33 | N35 | D97 | ka (1/Ms) | kd (1/s) | KD (M) | improvement |
| B18.5 | | D | | | Q | D | I | | F | I | | 1.09E+06 | 4.30E−04 | 3.95E−10 | 138.7 |
| B2.0 | | D | | | R | D | | R | F | I | T | 6.99E+06 | 3.15E−04 | 4.51E−11 | 1213.5 |
| B27.1 | | D | | | R | D | | | | T | T | 4.06E+06 | 7.42E−04 | 1.83E−10 | 299.3 |
| B32.5 | | | | | R | D | | | F | I | | 4.52E+06 | 4.68E−04 | 1.04E−10 | 528.4 |
| B41.2 | | D | | | R | D | | R | F | I | | 4.73E+06 | 2.45E−04 | 5.19E−11 | 1055.7 |
| B9.7 | | D | | | R | D | | R | | I | | 3.59E+06 | 3.34E−04 | 9.31E−11 | 588.2 |
| gB9.7 | E | D | S | Y | R | D | | R | | I | | 9.29E+05 | 1.85E−04 | 1.99E−10 | 275.4 |
| gB9.7-IgG | | D | S | Y | R | D | | R | | I | | 2.70E+06 | 2.36E−05 | 8.75E−12 | 6251.4 |
| 4B7 | | | | | | | | | | | | 3.15E+06 | 1.72E−01 | 5.47E−08 | 1 |

Example 6

Affinity-Improved Antibodies Showed More Potency in Restoring FXa Activity

To determine if affinity-improved anti-TFPI antibodies also improved their potency in restoring FXa activity by blocking the inhibitory effect of TFPI protein, we performed a FXa restoring assay. In this assay, a various indicated amount of the individual affinity-improved antibodies (30 μL) was incubated with the fixed amount of human, mouse or rat recombinant TFPI (20 μL, 6.6 nM) in a total reaction mixture of 50 μl for 30 min at room temperature. After incubation, 50 μL of FXa (3.39 nM) was added to the reaction mixture and incubated at 37° C. for 30 min. Then, 20 μL of Spectrozyme FXa substrate was added to the reaction mixture. After incubation of 12 min, the absorbance of each well was read at 405 nm using a plate reader (Molecular Device). For each experiment, a linear standard curve of the same amount of FXa (3.39 nM) inhibited by known amounts of TFPI was obtained. The 100% restored FXa activity was defined as the FXa activity without adding any amount of TFPI and 0% activity was defined as the FXa activity in the presence of TFPI protein (6.6 nM). The half maximal inhibitory concentration (IC50) was thus calculated for each individual anti-TFPI antibody, some of which are provided in Table 9. The half maximal effective concentration (EC50) was also calculated for selected 2A8 second-round variants and provided in Table 10.

TABLE 9

| IC50 and potency improvement for selected anti-TFPI antibodies with single amino acid substitutions using a FXa restoring assay as compared to their parental antibodies, 2A8 and 4B7, respectively. | | | |
|---|---|---|---|
| Sample | Clone | IC 50 (μg/mL) | Improvement |
| 2A8-2 | HC_S31P | 0.33 | 1.7 |
| 2A8-3 | HC_S31V | 0.201 | 3.5 |
| 2A8-4 | HC_S35D | 0.55 | 1.1 |
| 2A8-6 | HC_I51E | 0.76 | 0.9 |
| 2A8-7 | HC_S54F | 0.35 | 2.0 |
| 2A8-9 | HC_K99L | 0.181 | 3.9 |
| 2A8-10 | HC_K99V | 0.39 | 1.6 |
| 2A8-14 | LC_Y48F | 0.34 | 1.9 |
| 2A8-15 | LC_D91K | 0.34 | 1.9 |
| 2A8-16 | LC_D91L | 0.37 | 1.7 |
| 2A8-17 | LC_D91W | 0.23 | 3.0 |
| 2A8-20 | 2A8wt | 0.70 | 1.0 |
| 4B7HcD62R | HC_D62R | 0.058 | 25 |
| 4B7 | 4B7wt | 1.46 | 1.0 |

TABLE 10

EC50 and fold improvement for the selected anti-TFPI antibodies having multiple amino acid substitutions as compared to the parental 2A8.

| | 2A8 HC | | | | | 2A8 LC | | | | | EC50 | |
|---|---|---|---|---|---|---|---|---|---|---|---|---|
| Samples | S31 | S35 | I51 | S55 | K99 | Y48 | N51 | G56 | D91 | V96 | (nM) | Improvement |
| 2A8-127 | | D | | | L | F | V | D | | W | 0.44 | 18.2 |
| 2A8-143 | | D | | R | L | F | V | | L | W | 0.50 | 15.8 |
| 2A8-200 | | D | | R | L | F | V | | W | | 0.81 | 9.7 |
| 2A8-216 | V | | D | R | V | F | | | L | W | 1.08 | 7.3 |
| 2A8-9 | | | | | L | | | | | | 1.00 | 7.9 |
| 2A8 wt | | | | | | | | | | | 7.91 | 1.00 |

Example 7

Affinity-Improved Antibodies Showed More Potency in Shortening Clotting Time in a dPT Assay To confirm if these affinity-improved antibodies also improved the potency in shortening clotting time, a dPT is carried out determining the effect of selected affinity-matured antibodies on clotting time using human hemophilia A plasma. The dPT assay is done essentially as described in Welsch et al. (Thrombosis Res., 1991, 64(2): 213-222). Briefly, human hemophilia A plasma (George King Biomedical) is prepared by mixing plasma with 0.1 volumes of control buffer (as a negative control) or indicated anti-TFPI antibodies. After incubation for 30 min at 25° C., each of the prepared plasma samples (100 µL) is combined with 100 µL of appropriately diluted (1:500 dilution) Simplastin (Biometieux) as a source of thromboplastin and 100 µL of 25 mM calcium chloride. The clotting time is determined using a fibrometer STA4 (Stago) right after adding calcium chloride.

Example 8

Affinity-Improved Antibodies Showed More Potency in Shortening Whole Blood Clotting Time Using Anti-Factor Viii Antibody-Induced Human Hemophilia A Blood To confirm if affinity-improved antibodies show more potency in shortening clotting time, we used a ROTEM system to test the effect of these antibodies on clotting time in human FVIII-neutralizing antibody-induced hemophilia A blood, which mimics the blood from hemophilia A patients with inhibitors. The ROTEM system (Pentapharm GmbH) includes a four-channel instrument, a computer, plasma standards, activators and disposable cups and pins. Thrombelastographic parameters of ROTEM hemostasis systems includes: Clotting Time (CT), which reflects the reaction time (the time required to obtain 2 mm amplitude following the initiation of data collection) to initiate blood clotting; Clot Formation Time (CFT) and the alpha angle to reflect clotting propagation, and the maximum amplitude and the maximum elastic modulus to reflect clot firmness. In a ROTEM assay, 300 µl of freshly drawn citrated whole blood, in which the FVIII activity was neutralized by addition of polyclonal antibodies against FVIII, was used to test the effect of affinity-improved anti-TFPI antibodies as compared to the parental anti-TFPI antibodies. All constituents were reconstituted and mixed according to the manufacturer's instructions, with data collection for the time period required for each system. Briefly, samples were mixed by withdrawing/dispensing 300 µl of blood or plasma with an automated pipette into ROTEM cups with 20 µl of CaCl$_2$ (200 mmol) added, followed immediately by mixing of the sample and initiation of data collection. Data were collected for 2 hours using a computer-controlled (software version 2.96) ROTEM system.

Figure 2:
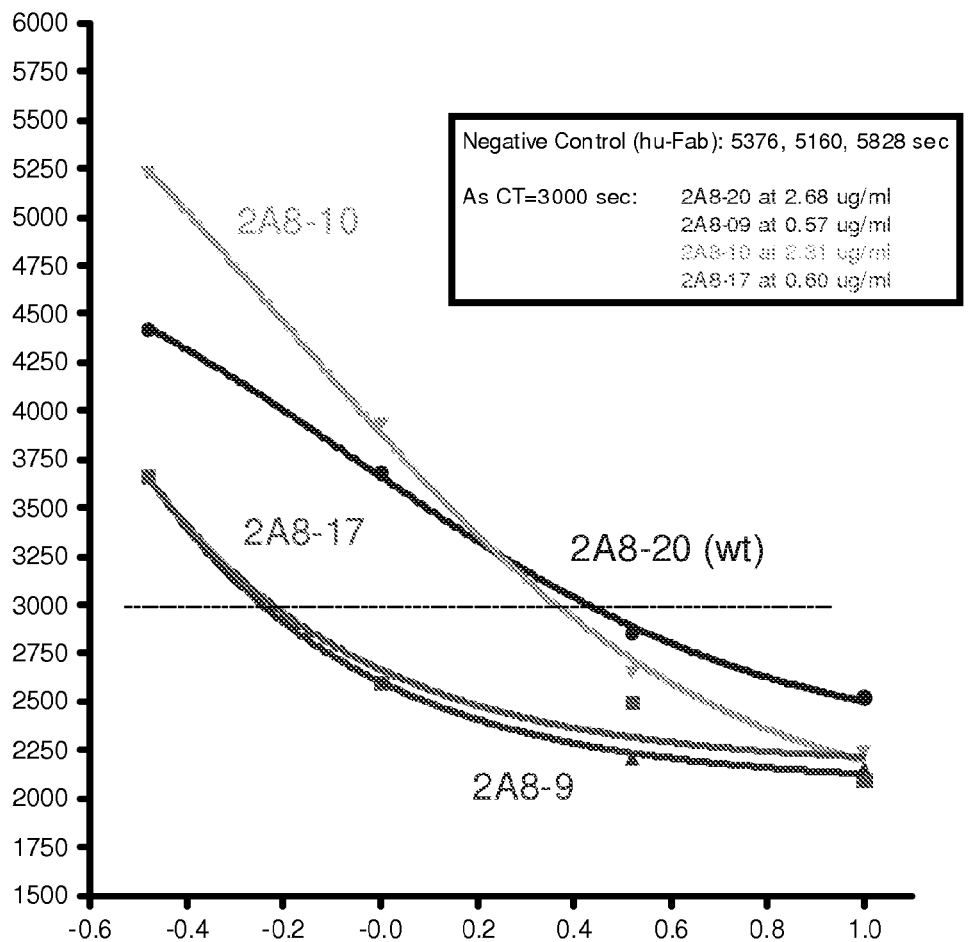
FIG. 2 depicts a graph showing the effect of selected single amino acid mutated anti-TFPI antibodies on clotting time of anti-factor VIII antibody-induced human hemophilic blood.
Figure 3:
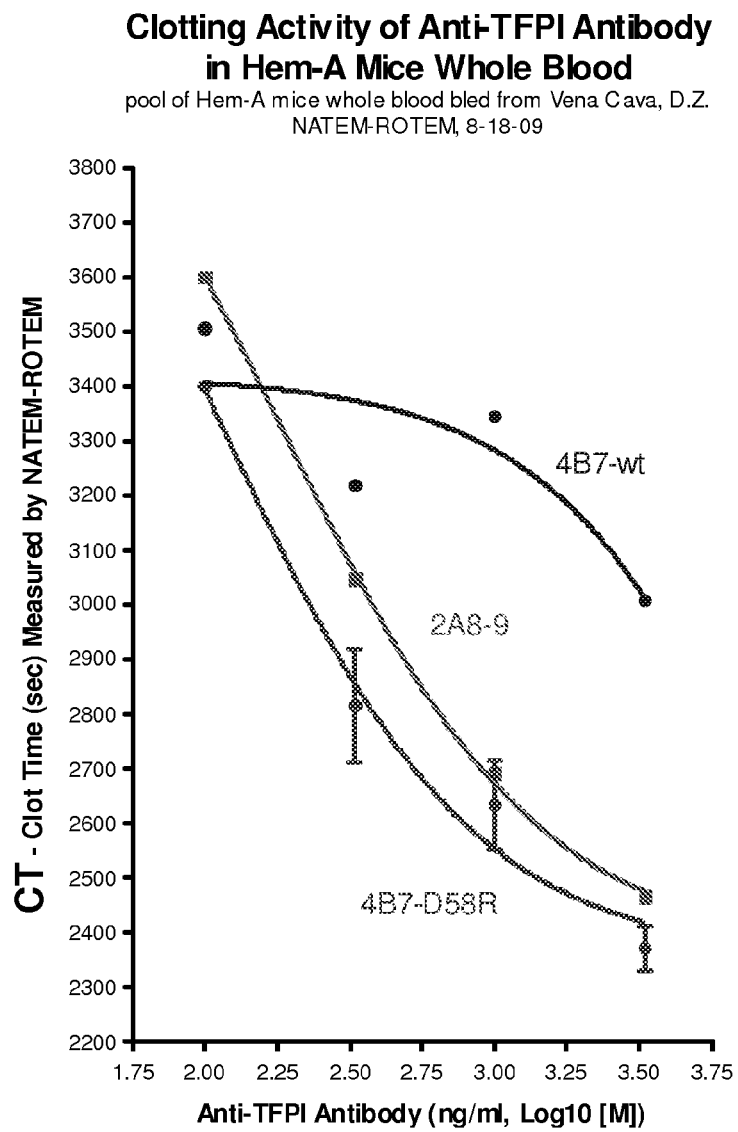
FIG. 3 depicts a graph showing that 4B7-D62R has much more potency in shortening clotting time in human antibody-induced hemophilia A blood as compared to the parental 4B7 antibody and to a less degree, as compared to single amino acid substitutions within 2A8.

An exemplary result of ROTEM assay in detecting the effect of affinity-improved anti-TFPI antibodies in shortening blood clotting time is shown in FIGS. 2 and 3. FIG. 2 shows the effect of selected first round affinity-maturated anti-TFPI antibodies on clotting time of human antibody-induced hemophilia blood. The much affinity-improved antibodies, 2A8-9 and 2A8-17 shows much more potency in shortening clotting time in human antibody-induced hemophilia A blood, whereas 2A8-10, whose binding affinity to TFPI was not improved, remained a similar clotting potency, as compared to the parental 2A8 antibody.

Example 9

Affinity-Improved Antibodies Show Better Survival Rate in a Tail-Vein-Transection Model of Hemophilia A Mice To determine if affinity-improved antibodies are more potency in a protective effect on bleeding mice, a tail-vein-transection model of hemophilia A mice was used. Mice were dosed via tail vein infusion with a various indicated amount of the parental anti-TFPI antibody 2A8 or the various indicated amount of A200, 24 hr prior to the injury. At 24 hours post-dosing, the left vein of the tail at 2.7 mm from the tip (in diameter) was transected. Survival was observed over 24 hours post transection. Survival rate was demonstrated to be dose-dependent when given with recombinant FVIII (10 IU/kg to 30 IU/kg).

Figure 4:
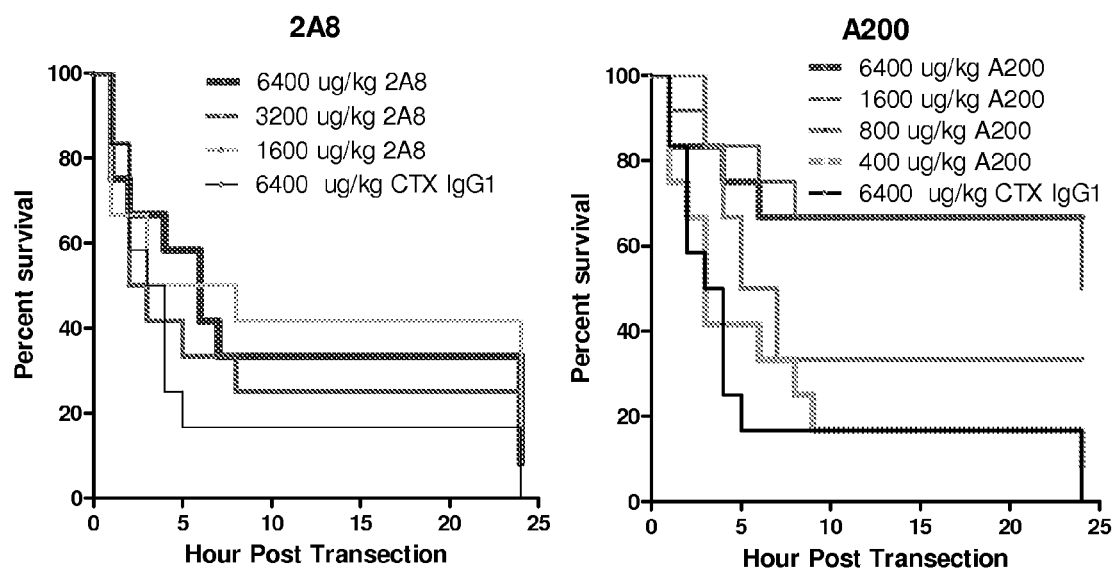
FIG. 4 depicts two graphs showing survival of hemophilia A mice treated with the parental antibody 2A8 and a 2A8 variant having multiple amino acid substitutions (A200) in a dose-dependent manner as compared to control mouse IgG1 (CTX IgG1).

FIG. 4 shows that a selected affinity-improved antibody A200 significantly prolonged the survival of hemophilia A mice in a dose-dependent manner as compared to control mouse IgG1 (CTX IgG1), and displayed a better survival rate than the parental antibody 2A8 at each of the equivalent doses.

Example 10

Figure 5:
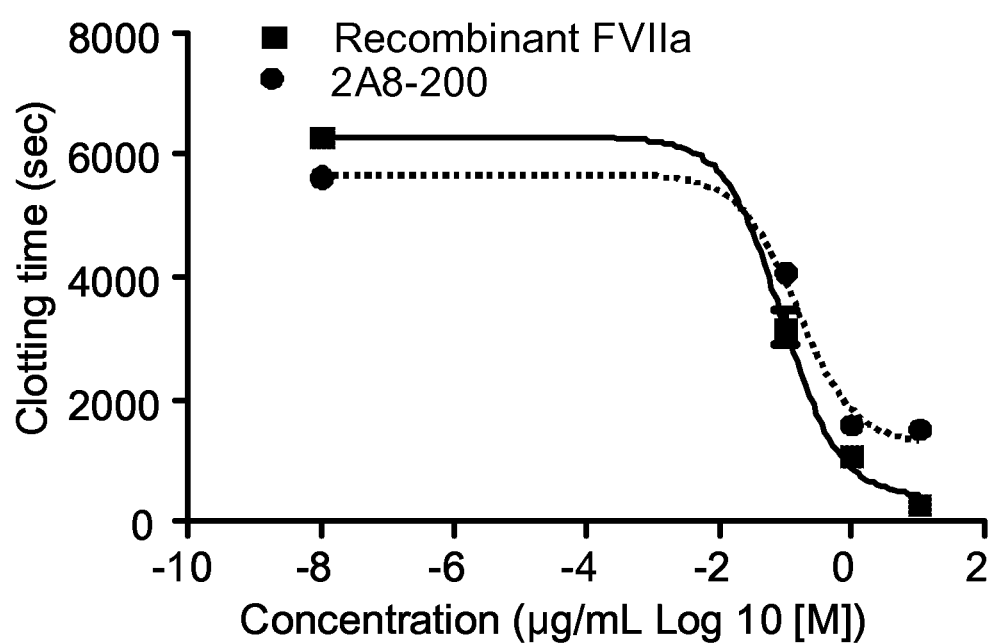
FIG. 5 depicts a graph showing that a 2A8 variant enhanced clotting in human hemophilia C (FXI-deficient) plasma in a dose-dependent manner and its effects were comparable to those of recombinant FVIIa.

Affinity-Improved Antibodies Showed Enhanced Clotting Using Human Hemophilia C (FXI-Deficient) Plasma Further, a ROTEM assay was utilized to test the effect of the antibodies on clotting time in human Factor XI deficient (FXI-deficient) plasma, which mimics the hemophilia C patients. The result of this ROTEM assay in detecting the effect of affinity-improved anti-TFPI antibodies in shortening plasma clotting time is shown in FIG. 5. FIG. 5 shows that a 2A8 variant, 2A8-200, enhanced clotting in human hemophilia C plasma in a dose-dependent manner and its effects are comparable to those of recombinant FVIIa.

While the present invention has been described with reference to the specific embodiments and examples, it should be understood that various modifications and changes may be made and equivalents may be substituted without departing from the true spirit and scope of the invention. The specification and examples are, accordingly, to be regarded in an illustrative rather then a restrictive sense. Furthermore, all articles, books, patent applications and patents referred to herein are incorporated herein by reference in their entireties.

We claim:

1. An isolated human monoclonal IgG antibody that binds specifically to human tissue factor pathway (TFPI) inhibitor, wherein the antibody comprises at least one amino acid substitution:
   (a) a human heavy chain comprising:
      a CDR 1 region with the amino acid sequence shown in SEQ ID NO: 41, optionally comprising a substitution at N32 relative to SEQ ID NO: 3;
      a CDR2 region with the amino acid sequence shown in SEQ ID NO: 42, optionally comprising a substitution selected from the group consisting of K55 and D62 relative to SEQ ID NO: 3;
      a CDR3 region that binds specifically to TFPI and has the amino acid sequence shown in SEQ ID NO: 43 optionally comprising a substitution at Y112 relative to SEQ ID NO: 3, and
      optionally, an amino acid substitution at G44 relative to SEQ ID NO: 3;
   (b) a human light chain comprising:
      a CDR1 region with the amino acid sequence shown in SEQ ID NO: 44, optionally comprising a substitution of a position selected from the group consisting of S32 and N35 and combinations thereof relative to SEQ ID NO: 4;
      a CDR2 region with the amino acid sequence shown in SEQ ID NO: 45;
      a CDR3 region that binds specifically to TFPI and has the amino acid sequence shown in SEQ ID NO: 46.

2. An isolated human monoclonal IgG antibody that binds specifically to human tissue factor pathway inhibitor (TFPI), wherein the antibody comprises:
   (a) a human heavy chain comprising:
      a CDR 1 region with the amino acid sequence shown in SEQ ID NO: 41, comprising a substitution of N32 relative to SEQ ID NO: 3,
      a CDR2 region with the amino acid sequence shown in SEQ ID NO: 42, comprising at least one substitution relative to SEQ ID NO: 3 selected from the group consisting of K55Y and D62R and combinations thereof;
      a CDR3 region that binds specifically to TFPI and has the amino acid sequence shown in SEQ ID NO: 43 comprising a substitution relative to SEQ ID NO: 43 of Y112D relative to SEQ ID NO: 3, and
   a substitution relative to SEQ ID No. 3 of G44S; and
   (b) a human light chain comprising:
      a CDR1 region with the amino acid sequence shown in SEQ ID NO: 44, comprising at least one substitution selected from the group consisting of S32R and N35I relative to SEQ ID NO: 4 and combinations thereof;
      a CDR2 region with the amino acid sequence shown in SEQ ID NO: 45,
      a CDR3 region that binds specifically to TFPI and has the amino acid sequence shown in SEQ ID NO: 46.

3. The antibody of claim 1 wherein the substitution at N32 is N32D.

4. The antibody of claim 1 wherein the substitution of K55 is K55Y.

5. The antibody of claim 1 wherein the substitution of G44 is G44S.

6. The antibody of claim 1 wherein the substitution of D62 is D62R.

7. The antibody of claim 1 wherein the substitution of Y112 is Y112D.

8. The antibody of claim 1 wherein the substitution of S32 is S32R.

9. The antibody of claim 1 wherein the substitution of N35 is N35I.

10. The antibody of claim 1, wherein the amino at position 51 of the heavy chain relative to SEQ ID NO: 3 is Q.

* * * * *

```
                        SEQUENCE LISTING

<160> NUMBER OF SEQ ID NOS: 46

<210> SEQ ID NO 1
<211> LENGTH: 117
<212> TYPE: PRT
<213> ORGANISM: Homo sapiens

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

Ser Ser Ile Arg Gly Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Tyr Arg Tyr Trp Phe Asp Tyr Trp Gly Gln Gly Thr Leu
            100                 105                 110

Val Thr Val Ser Ser
        115

<210> SEQ ID NO 2
<211> LENGTH: 108
<212> TYPE: PRT
<213> ORGANISM: Homo sapiens

<400> SEQUENCE: 2

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Tyr
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Asp Gly Val Pro Val
                85                  90                  95

Phe Gly Gly Gly Thr Lys Leu Thr Val Leu Gly Gln
            100                 105

<210> SEQ ID NO 3
<211> LENGTH: 123
<212> TYPE: PRT
<213> ORGANISM: Homo sapiens

<400> SEQUENCE: 3
```

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
             20                  25                  30

Ser Ala Ala Trp Ser Trp Ile Arg Gln Ser Pro Gly Arg Gly Leu Glu
         35                  40                  45

Trp Leu Gly Ile Ile Tyr Lys Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
             85                  90                  95

Tyr Tyr Cys Ala Arg Trp His Ser Asp Lys His Trp Gly Phe Asp Tyr
            100                 105                 110

Trp Gly Gln Gly Thr Leu Val Thr Val Ser Ser
            115                 120
```

<210> SEQ ID NO 4
<211> LENGTH: 114
<212> TYPE: PRT
<213> ORGANISM: Homo sapiens

<400> SEQUENCE: 4

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Phe Ser
             20                  25                  30

Asp Gly Asn Thr Tyr Leu Asn Trp Tyr Leu Gln Lys Pro Gly Gln Ser
         35                  40                  45

Pro Gln Leu Leu Ile Tyr Lys Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
             85                  90                  95

Asp Ser Tyr Pro Leu Thr Phe Gly Gln Gly Thr Lys Val Glu Ile Lys
            100                 105                 110

Arg Thr
```

<210> SEQ ID NO 5
<211> LENGTH: 117
<212> TYPE: PRT
<213> ORGANISM: Artificial
<220> FEATURE:
<223> OTHER INFORMATION: Variant

<400> SEQUENCE: 5

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Tyr
             20                  25                  30

Gly Met Asp Trp Val Arg Gln Ala Pro Gly Lys Gly Leu Glu Trp Val
         35                  40                  45

Ser Ser Ile Arg Gly Ser Ser Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 6
<211> LENGTH: 117
<212> TYPE: PRT
<213> ORGANISM: Artificial
<220> FEATURE:
<223> OTHER INFORMATION: Variant

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
            35                  40                  45

Ser Ser Ile Arg Gly Ser Arg Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 7
<211> LENGTH: 117
<212> TYPE: PRT
<213> ORGANISM: Artificial
<220> FEATURE:
<223> OTHER INFORMATION: Variant

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
            35                  40                  45

Ser Ser Ile Arg Gly Ser Arg Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

```
<210> SEQ ID NO 8
<211> LENGTH: 117
<212> TYPE: PRT
<213> ORGANISM: Artificial
<220> FEATURE:
<223> OTHER INFORMATION: Variant

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
            20                  25                  30

Gly Met Ser Trp Val Arg Gln Ala Pro Gly Lys Gly Leu Glu Trp Val
        35                  40                  45

Ser Ser Asp Arg Gly Ser Arg Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Arg Tyr Trp Phe Asp Tyr Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: Artificial
<220> FEATURE:
<223> OTHER INFORMATION: Variant

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Artificial
<220> FEATURE:
<223> OTHER INFORMATION: Variant

<400> SEQUENCE: 10

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
        20                  25                  30

Gly Met Asp Trp Val Arg Gln Ala Pro Gly Lys Gly Leu Glu Trp Val
            35                  40                  45

Ser Ser Ile Arg Gly Ser Arg Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115
```

```
<210> SEQ ID NO 11
<211> LENGTH: 117
<212> TYPE: PRT
<213> ORGANISM: Artificial
<220> FEATURE:
<223> OTHER INFORMATION: Variant

<400> SEQUENCE: 11
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
        20                  25                  30

Gly Met Ser Trp Val Arg Gln Ala Pro Gly Lys Gly Leu Glu Trp Val
            35                  40                  45

Ser Ser Asp Arg Gly Ser Arg Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Arg Tyr Trp Phe Asp Tyr Trp Gly Gln Gly Thr Leu
            100                 105                 110

Val Thr Val Ser Ser
        115
```

```
<210> SEQ ID NO 12
<211> LENGTH: 108
<212> TYPE: PRT
<213> ORGANISM: Artificial
<220> FEATURE:
<223> OTHER INFORMATION: Variant

<400> SEQUENCE: 12
```

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
        20                  25                  30

His Trp Tyr Gln Gln Lys Pro Gly Gln Ala Pro Val Val Val Ile Phe
            35                  40                  45

Tyr Asp Val Asn Arg Pro Ser Asp Ile Pro Glu Arg Phe Ser Gly Ser
50                  55                  60

Asn Ser Gly Asn Thr Ala Thr Leu Thr Ile Ser Gly Thr Gln Ala Glu
```

```
65                  70                  75                  80

Asp Glu Ala Asp Tyr Tyr Cys Gln Ser Trp Asp Asp Gly Val Pro Trp
                85                  90                  95

Phe Gly Gly Gly Thr Lys Leu Thr Val Leu Gly Gln
            100                 105

<210> SEQ ID NO 13
<211> LENGTH: 108
<212> TYPE: PRT
<213> ORGANISM: Artificial
<220> FEATURE:
<223> OTHER INFORMATION: Variant

<400> SEQUENCE: 13

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Leu Asp Gly Val Pro Trp
                85                  90                  95

Phe Gly Gly Gly Thr Lys Leu Thr Val Leu Gly Gln
            100                 105

<210> SEQ ID NO 14
<211> LENGTH: 108
<212> TYPE: PRT
<213> ORGANISM: Artificial
<220> FEATURE:
<223> OTHER INFORMATION: Variant

<400> SEQUENCE: 14

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Trp Asp Gly Val Pro Val
                85                  90                  95

Phe Gly Gly Gly Thr Lys Leu Thr Val Leu Gly Gln
            100                 105

<210> SEQ ID NO 15
<211> LENGTH: 108
<212> TYPE: PRT
<213> ORGANISM: Artificial
<220> FEATURE:
<223> OTHER INFORMATION: Variant

<400> SEQUENCE: 15
```

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Phe
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Leu Asp Gly Val Pro Trp
                85                  90                  95

Phe Gly Gly Gly Thr Lys Leu Thr Val Leu Gly Gln
            100                 105

<210> SEQ ID NO 16
<211> LENGTH: 108
<212> TYPE: PRT
<213> ORGANISM: Artificial
<220> FEATURE:
<223> OTHER INFORMATION: Variant

<400> SEQUENCE: 16

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Phe
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Leu Asp Gly Val Pro Trp
                85                  90                  95

Phe Gly Gly Gly Thr Lys Leu Thr Val Leu Gly Gln
            100                 105

<210> SEQ ID NO 17
<211> LENGTH: 108
<212> TYPE: PRT
<213> ORGANISM: Artificial
<220> FEATURE:
<223> OTHER INFORMATION: Variant

<400> SEQUENCE: 17

Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Trp Ser Ser Thr Pro Val

Phe Gly Gly Gly Thr Lys Leu Thr Val Leu Gly Gln
            100                 105

<210> SEQ ID NO 18
<211> LENGTH: 108
<212> TYPE: PRT
<213> ORGANISM: Artificial
<220> FEATURE:
<223> OTHER INFORMATION: Variant

<400> SEQUENCE: 18

Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Leu Ser Gly Thr Pro Trp
                85                  90                  95

Phe Gly Gly Gly Thr Lys Leu Thr Val Leu Gly Gln
            100                 105

<210> SEQ ID NO 19
<211> LENGTH: 123
<212> TYPE: PRT
<213> ORGANISM: Artificial
<220> FEATURE:
<223> OTHER INFORMATION: Variant

<400> SEQUENCE: 19

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Gln Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 20
<211> LENGTH: 123
<212> TYPE: PRT
<213> ORGANISM: Artificial
<220> FEATURE:
<223> OTHER INFORMATION: Variant

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 21
<211> LENGTH: 123
<212> TYPE: PRT
<213> ORGANISM: Artificial
<220> FEATURE:
<223> OTHER INFORMATION: Variant

<400> SEQUENCE: 21

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 22
<211> LENGTH: 123
<212> TYPE: PRT
<213> ORGANISM: Artificial
<220> FEATURE:
<223> OTHER INFORMATION: Variant

<400> SEQUENCE: 22

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala

```
                50                  55                  60
Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp His Ser Asp Lys His Trp Gly Phe Asp Asp
                100                 105                 110

Trp Gly Gln Gly Thr Leu Val Thr Val Ser Ser
            115                 120

<210> SEQ ID NO 23
<211> LENGTH: 123
<212> TYPE: PRT
<213> ORGANISM: Artificial
<220> FEATURE:
<223> OTHER INFORMATION: Variant

<400> SEQUENCE: 23

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asp
                 20                  25                  30

Ser Ala Ala Trp Ser Trp Ile Arg Gln Ser Pro Gly Arg Gly Leu Glu
                 35                  40                  45

Trp Leu Gly Ile Ile Tyr Lys Arg Ser Lys Trp Tyr Asn Arg Tyr Ala
             50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp His Ser Asp Lys His Trp Gly Phe Asp Asp
                100                 105                 110

Trp Gly Gln Gly Thr Leu Val Thr Val Ser Ser
            115                 120

<210> SEQ ID NO 24
<211> LENGTH: 123
<212> TYPE: PRT
<213> ORGANISM: Artificial
<220> FEATURE:
<223> OTHER INFORMATION: Variant

<400> SEQUENCE: 24

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asp
                 20                  25                  30

Ser Ala Ala Trp Ser Trp Ile Arg Gln Ser Pro Gly Arg Gly Leu Glu
                 35                  40                  45

Trp Leu Gly Ile Ile Tyr Lys Arg Ser Lys Trp Tyr Asn Arg Tyr Ala
             50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp His Ser Asp Lys His Trp Gly Phe Asp Asp
                100                 105                 110
```

```
Trp Gly Gln Gly Thr Leu Val Thr Val Ser Ser
        115                 120

<210> SEQ ID NO 25
<211> LENGTH: 123
<212> TYPE: PRT
<213> ORGANISM: Artificial
<220> FEATURE:
<223> OTHER INFORMATION: Variant

<400> SEQUENCE: 25

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Ser Arg Gly Leu Glu
        35                  40                  45

Trp Leu Gly Ile Ile Tyr Tyr Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 26
<211> LENGTH: 123
<212> TYPE: PRT
<213> ORGANISM: Artificial
<220> FEATURE:
<223> OTHER INFORMATION: Variant

<400> SEQUENCE: 26

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Ser Arg Gly Leu Glu
        35                  40                  45

Trp Leu Gly Ile Ile Tyr Tyr Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120

<210> SEQ ID NO 27
<211> LENGTH: 114
<212> TYPE: PRT
<213> ORGANISM: Artificial
<220> FEATURE:
<223> OTHER INFORMATION: Variant
```

<400> SEQUENCE: 27

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ile Ser
            20                  25                  30

Phe Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr
```

<210> SEQ ID NO 28
<211> LENGTH: 114
<212> TYPE: PRT
<213> ORGANISM: Artificial
<220> FEATURE:
<223> OTHER INFORMATION: Variant

<400> SEQUENCE: 28

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Phe Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Thr Ser Tyr Pro Leu Thr Phe Gly Gln Gly Thr Lys Val Glu Ile Lys
            100                 105                 110

Arg Thr
```

<210> SEQ ID NO 29
<211> LENGTH: 114
<212> TYPE: PRT
<213> ORGANISM: Artificial
<220> FEATURE:
<223> OTHER INFORMATION: Variant

<400> SEQUENCE: 29

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Ser
            20                  25                  30

Asp Gly Thr Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Thr Ser Tyr Pro Leu Thr Phe Gly Gln Gly Thr Lys Val Glu Ile Lys
            100                 105                 110

Arg Thr

<210> SEQ ID NO 30
<211> LENGTH: 114
<212> TYPE: PRT
<213> ORGANISM: Artificial
<220> FEATURE:
<223> OTHER INFORMATION: Variant

<400> SEQUENCE: 30

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Phe Ser
                 20                  25                  30

Phe Gly Ile Thr Tyr Leu Asn Trp Tyr Leu Gln Lys Pro Gly Gln Ser
             35                  40                  45

Pro Gln Leu Leu Ile Tyr Lys Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Asp Ser Tyr Pro Leu Thr Phe Gly Gln Gly Thr Lys Val Glu Ile Lys
            100                 105                 110

Arg Thr

<210> SEQ ID NO 31
<211> LENGTH: 114
<212> TYPE: PRT
<213> ORGANISM: Artificial
<220> FEATURE:
<223> OTHER INFORMATION: Variant

<400> SEQUENCE: 31

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Phe Arg
                 20                  25                  30

Phe Gly Ile Thr Tyr Leu Asn Trp Tyr Leu Gln Lys Pro Gly Gln Ser
             35                  40                  45

Pro Gln Leu Leu Ile Tyr Lys Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Asp Ser Tyr Pro Leu Thr Phe Gly Gln Gly Thr Lys Val Glu Ile Lys
            100                 105                 110

Arg Thr
```

```
<210> SEQ ID NO 32
<211> LENGTH: 114
<212> TYPE: PRT
<213> ORGANISM: Artificial
<220> FEATURE:
<223> OTHER INFORMATION: Variant

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Asp Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr

<210> SEQ ID NO 33
<211> LENGTH: 114
<212> TYPE: PRT
<213> ORGANISM: Artificial
<220> FEATURE:
<223> OTHER INFORMATION: Variant

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Asp Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr

<210> SEQ ID NO 34
<211> LENGTH: 114
<212> TYPE: PRT
<213> ORGANISM: Artificial
<220> FEATURE:
<223> OTHER INFORMATION: Variant

<400> SEQUENCE: 34

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
```

```
                20                  25                  30
Asp Gly Ile Thr Tyr Leu Asn Trp Tyr Leu Gln Lys Pro Gly Gln Ser
            35                  40                  45

Pro Gln Leu Leu Ile Tyr Lys Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Asp Ser Tyr Pro Leu Thr Phe Gly Gln Gly Thr Lys Val Glu Ile Lys
            100                 105                 110

Arg Thr

<210> SEQ ID NO 35
<211> LENGTH: 9
<212> TYPE: PRT
<213> ORGANISM: Homo sapiens
<220> FEATURE:
<221> NAME/KEY: MISC_FEATURE
<223> OTHER INFORMATION: CDR1 region of IgG heavy chain of 2A8 antibody

<400> SEQUENCE: 35

Phe Thr Phe Arg Ser Tyr Gly Met Ser
1               5

<210> SEQ ID NO 36
<211> LENGTH: 17
<212> TYPE: PRT
<213> ORGANISM: Homo sapiens
<220> FEATURE:
<221> NAME/KEY: MISC_FEATURE
<223> OTHER INFORMATION: CDR2 region of human IgG heavy chain of 2A8
      antibody

<400> SEQUENCE: 36

Ser Ile Arg Gly Ser Ser Ser Thr Tyr Tyr Ala Asp Ser Val Lys
1               5                   10                  15

Gly

<210> SEQ ID NO 37
<211> LENGTH: 8
<212> TYPE: PRT
<213> ORGANISM: Homo sapiens
<220> FEATURE:
<221> NAME/KEY: MISC_FEATURE
<223> OTHER INFORMATION: CDR3 region of human IgG heavy chain of 2A8
      antibody

<400> SEQUENCE: 37

Lys Tyr Arg Tyr Trp Phe Asp Tyr
1               5

<210> SEQ ID NO 38
<211> LENGTH: 11
<212> TYPE: PRT
<213> ORGANISM: Homo sapiens
<220> FEATURE:
<221> NAME/KEY: MISC_FEATURE
<223> OTHER INFORMATION: CDR1 region of human IgG light chain of 2A8
      antibody

<400> SEQUENCE: 38

Ser Gly Asp Asn Leu Arg Asn Tyr Tyr Ala His
1               5                   10
```

<210> SEQ ID NO 39
<211> LENGTH: 8
<212> TYPE: PRT
<213> ORGANISM: Homo sapiens
<220> FEATURE:
<221> NAME/KEY: MISC_FEATURE
<223> OTHER INFORMATION: CDR2 region of IgG light chain of 2A8 antibody

<400> SEQUENCE: 39

Tyr Tyr Asp Asn Asn Arg Pro Ser
1               5

<210> SEQ ID NO 40
<211> LENGTH: 9
<212> TYPE: PRT
<213> ORGANISM: Homo sapiens
<220> FEATURE:
<221> NAME/KEY: MISC_FEATURE
<223> OTHER INFORMATION: CDR3 region of IgG light chain of 2A8 antibody

<400> SEQUENCE: 40

Gln Ser Trp Asp Asp Gly Val Pro Val
1               5

<210> SEQ ID NO 41
<211> LENGTH: 11
<212> TYPE: PRT
<213> ORGANISM: Homo sapiens
<220> FEATURE:
<221> NAME/KEY: MISC_FEATURE
<223> OTHER INFORMATION: CDR1 region of IgG heavy chain of 4B7 antibody

<400> SEQUENCE: 41

Asp Ser Val Ser Ser Asn Ser Ala Ala Trp Ser
1               5                   10

<210> SEQ ID NO 42
<211> LENGTH: 18
<212> TYPE: PRT
<213> ORGANISM: Homo sapiens
<220> FEATURE:
<221> NAME/KEY: MISC_FEATURE
<223> OTHER INFORMATION: CDR2 region of IgG heavy chain of 4B7 antibody

<400> SEQUENCE: 42

Ile Ile Tyr Lys Arg Ser Lys Trp Tyr Asn Asp Tyr Ala Val Ser Val
1               5                   10                  15

Lys Ser

<210> SEQ ID NO 43
<211> LENGTH: 11
<212> TYPE: PRT
<213> ORGANISM: Homo sapiens
<220> FEATURE:
<221> NAME/KEY: MISC_FEATURE
<223> OTHER INFORMATION: CDR3 region of IgG heavy chain of 4B7 antibody

<400> SEQUENCE: 43

Trp His Ser Asp Lys His Trp Gly Phe Asp Tyr
1               5                   10

<210> SEQ ID NO 44
<211> LENGTH: 16
<212> TYPE: PRT
<213> ORGANISM: Homo sapiens
<220> FEATURE:

```
<221> NAME/KEY: MISC_FEATURE
<223> OTHER INFORMATION: CDR1 region of IgG light chain of 4B7 antibody

<400> SEQUENCE: 44

Arg Ser Ser Gln Ser Leu Val Phe Ser Asp Gly Asn Thr Tyr Leu Asn
1               5                   10                  15

<210> SEQ ID NO 45
<211> LENGTH: 7
<212> TYPE: PRT
<213> ORGANISM: Homo sapiens
<220> FEATURE:
<221> NAME/KEY: MISC_FEATURE
<223> OTHER INFORMATION: CDR2 region of IgG light chain of 4B7 antibody

<400> SEQUENCE: 45

Lys Gly Ser Asn Arg Ala Ser
1               5

<210> SEQ ID NO 46
<211> LENGTH: 9
<212> TYPE: PRT
<213> ORGANISM: Homo sapiens
<220> FEATURE:
<221> NAME/KEY: MISC_FEATURE
<223> OTHER INFORMATION: CDR3 region of IgG light chain of 4B7 antibody

<400> SEQUENCE: 46

Gln Gln Tyr Asp Ser Tyr Pro Leu Thr
1               5
```